(12) United States Patent
Gollinger et al.

(10) Patent No.: US 11,957,587 B2
(45) Date of Patent: *Apr. 16, 2024

(54) PROTECTED ADJUSTABLE HEART VALVE SIZER

(71) Applicant: Edwards Lifesciences Corporation, Irvine, CA (US)

(72) Inventors: Gerald B. Gollinger, Rancho Santa Margarita, CA (US); William A. Maywald, Santa Ana, CA (US); Derrick Johnson, Orange, CA (US); Brian S. Conklin, Orange, CA (US); Ankita Bordoloi Gurunath, Irvine, CA (US); Da-Yu Chang, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/454,035

(22) Filed: Nov. 8, 2021

(65) Prior Publication Data

US 2022/0061992 A1 Mar. 3, 2022

Related U.S. Application Data

(63) Continuation of application No. 15/899,355, filed on Feb. 19, 2018, now Pat. No. 11,166,819, which is a continuation of application No. 14/315,649, filed on Jun. 26, 2014, now Pat. No. 9,895,228.

(60) Provisional application No. 61/897,165, filed on Oct. 29, 2013, provisional application No. 61/841,168, filed on Jun. 28, 2013.

(51) Int. Cl.
*A61F 2/24* (2006.01)
*A61B 5/107* (2006.01)

(52) U.S. Cl.
CPC .......... *A61F 2/2496* (2013.01); *A61B 5/1076* (2013.01)

(58) Field of Classification Search
CPC ........................... A61F 2/2496; A61B 5/1076
See application file for complete search history.

(56) References Cited

U.S. PATENT DOCUMENTS

| | | |
|---|---|---|
| 5,489,296 A | 2/1996 | Love et al. |
| 7,007,396 B2 | 3/2006 | Rudko et al. |
| 7,258,698 B2 | 8/2007 | Lemmon |
| 2003/0191416 A1 | 10/2003 | Rosenman et al. |
| 2013/0150954 A1 | 6/2013 | Conklin |

*Primary Examiner* — Devin B Henson
*Assistant Examiner* — Jonathan M Haney
(74) *Attorney, Agent, or Firm* — Guy Cumberbatch

(57) ABSTRACT

A heart valve sizer and sizer cover are provided for determining the size of a heart valve annulus. The valve sizer can include a handle, a shaft extending distally from the handle, a sizing element coupled to the distal end of the shaft, the sizing element being movable between a first retracted position and a second expanded position, and a sizer cover. The sizer cover can be formed from a continuous sheet of material configured to surround at least a portion of the sizing element of the heart valve sizer so as to guard against entanglement of the sizing element with structures of a human heart.

20 Claims, 17 Drawing Sheets

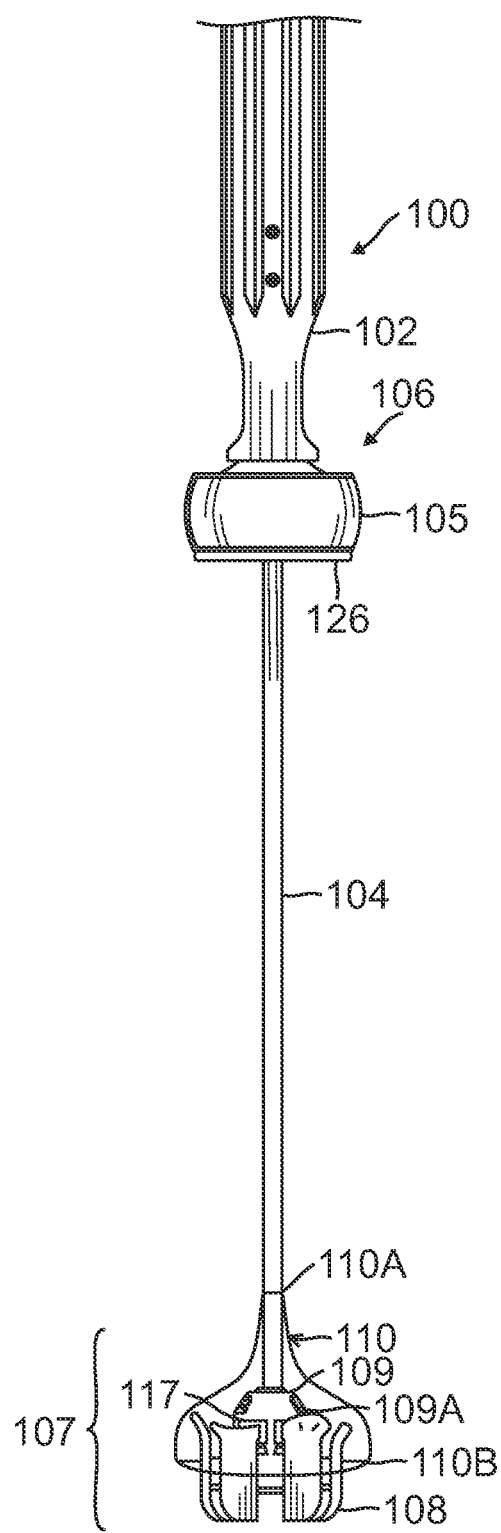
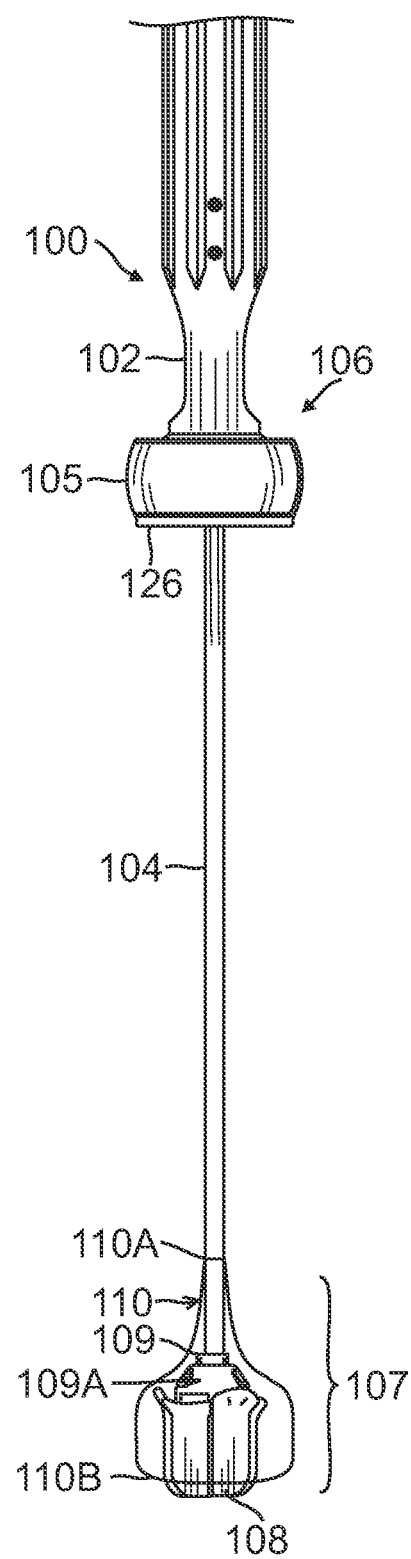
FIG. 1C
FIG. 1D

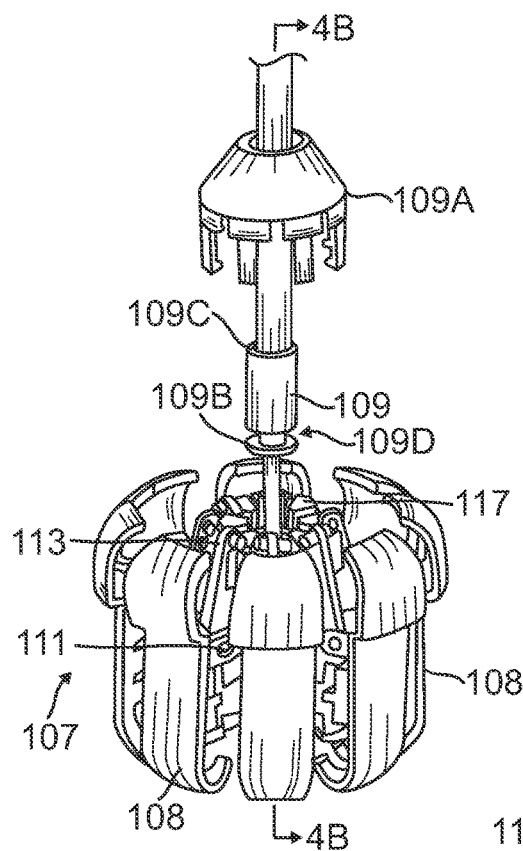
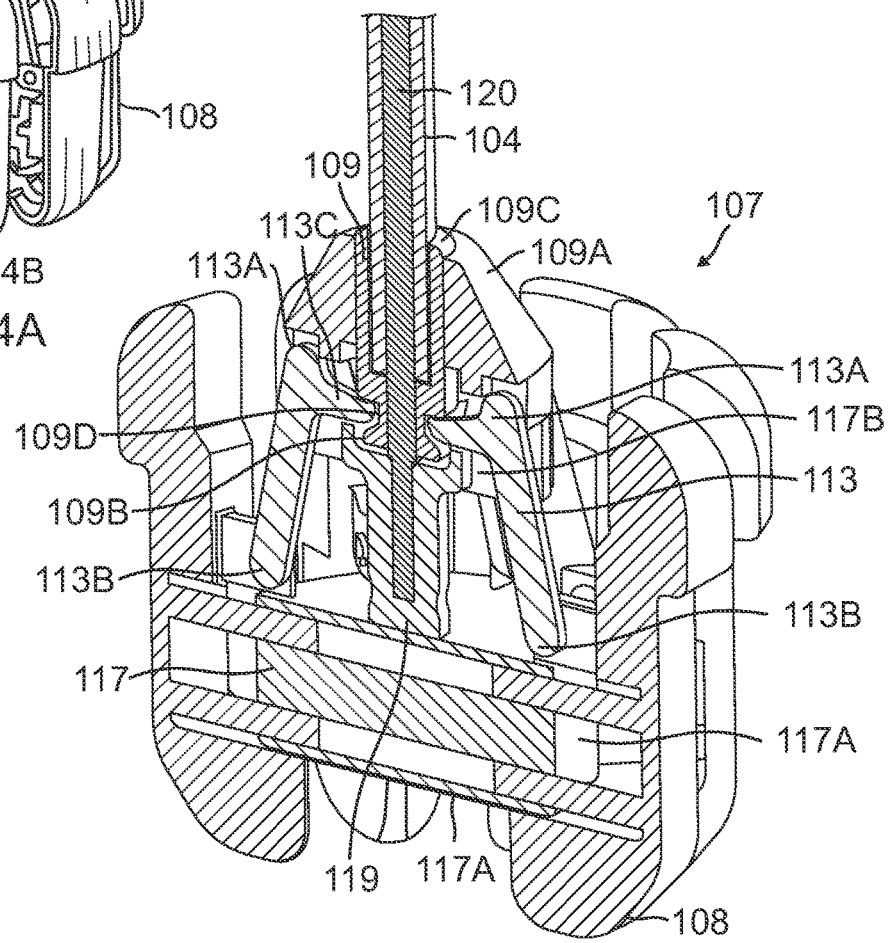
FIG. 4A
FIG. 4B

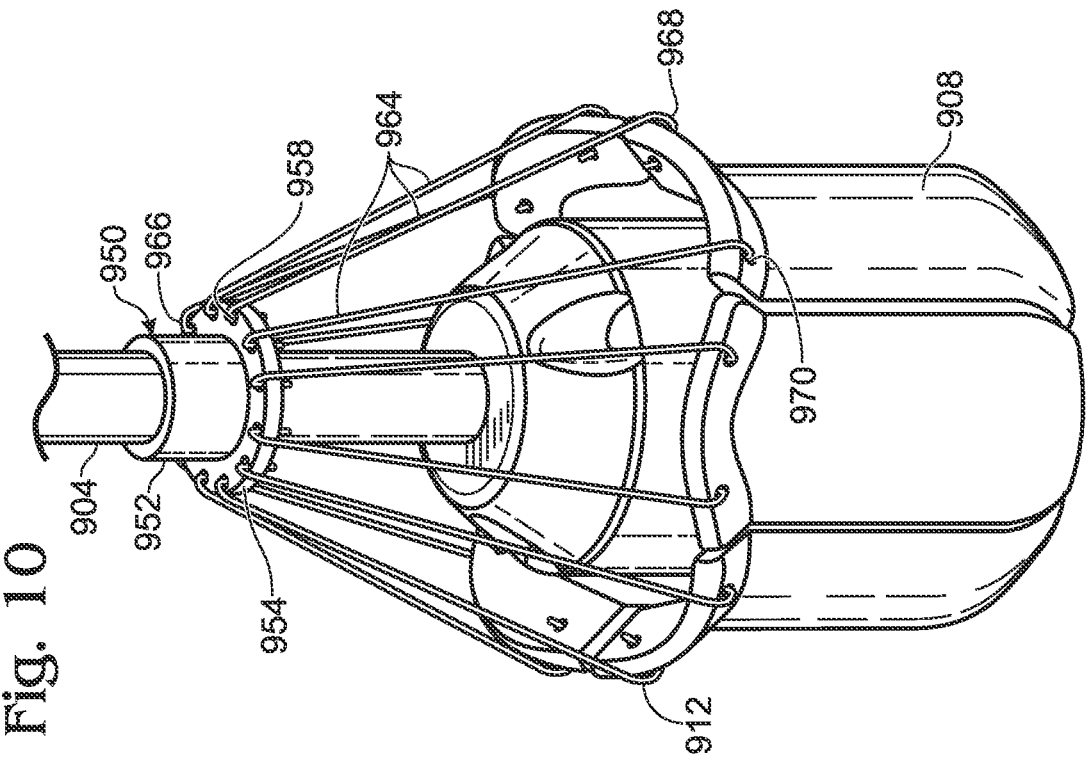
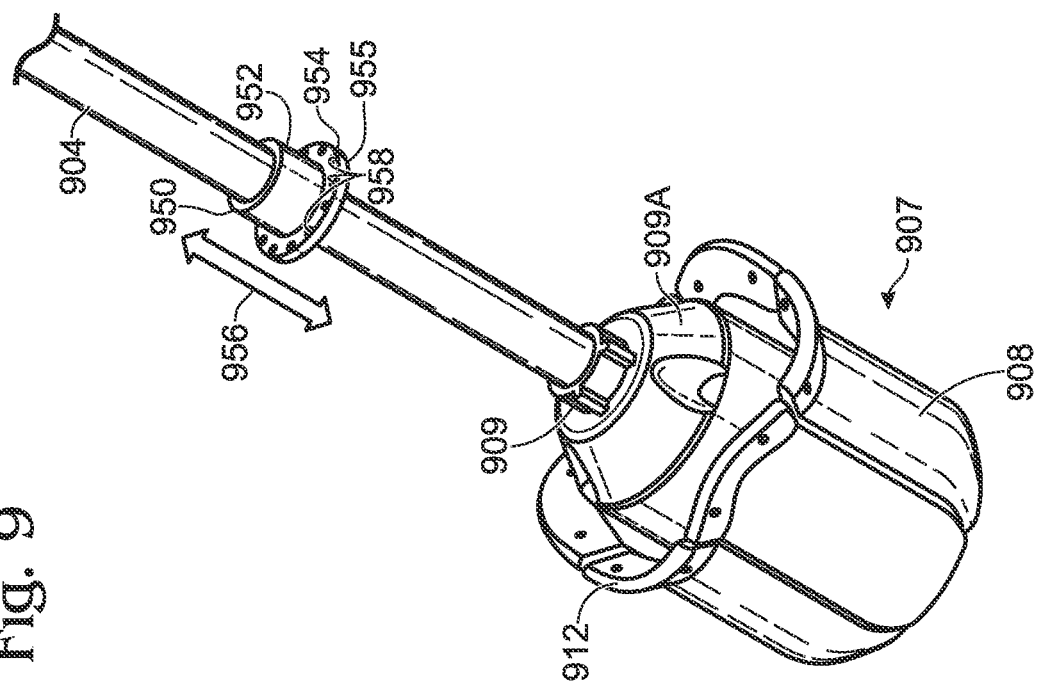

PROTECTED ADJUSTABLE HEART VALVE SIZER

CROSS REFERENCE TO RELATED APPLICATIONS

This application is a continuation of U.S. application Ser. No. 15/899,355, filed Feb. 19, 2018, now U.S. Pat. No. 11,166,819, which is a continuation of U.S. application Ser. No. 14/315,649, filed Jun. 26, 2014, now U.S. Pat. No. 9,895,228, which claims the benefit of U.S. Application No. 61/897,165, filed Oct. 29, 2013 and the benefit of U.S. Application No. 61/841,168, filed Jun. 28, 2013, the entire disclosures all of which are incorporated by reference for all purposes.

FIELD OF THE INVENTION

The present disclosure is directed to an apparatus for accurately determining a size of a heart valve annulus using a heart valve sizer. More particularly, the present disclosure relates to a heart valve sizer and sizer cover that prevents entanglement and improves smoothness of insertion and removal while accessing the valvular and sub-valvular spaces of the heart.

BACKGROUND OF THE DISCLOSURE

A successful valve replacement or annuloplasty surgery requires accurate measurement of the size of the valve annulus. One of the conventional ways of measuring the valve annulus involves using sizer discs that resemble the shape of the valve annulus, which are provided in various incremental sizes corresponding to the stepped replacement valve sizes. In use, the sizer disc is connected to a rod and is guided into the patient's valve annulus and the surgeon checks the fit of the disc within the valve annulus. If the surgeon is not satisfied with the fit, the surgeon removes the disc from the body and inserts a new disc of a different size into the valve annulus. Once the size of the native annulus is determined, a properly sized replacement valve or annuloplasty device is selected and implanted. This is a time-consuming method and therefore adds to the overall surgery time. Further, the determination of the appropriate size is based on the feeling of the surgeon rather than any mechanical feature, and may not be accurate in some instances.

Alternatively, another conventional way of measuring the valve annulus involves using a heart valve sizer which is introduced into the patient only once. The sizer is capable of gauging a number of appropriate replacement valve or annuloplasty device sizes. These sizers are dimensionally the same as the replacement valves they represent. Due to size constraints, insertion of such heart valve sizers may be a hindrance for certain procedures, especially for minimally invasive surgical incisions such as thoracotomies. With minimally invasive surgical (MIS) type procedures performed through small surgical incisions, the surgeon may not have a good approach angle to the native annulus, thus hindering an accurate tactile feedback to the surgeon when the sizer is in place.

In determining the optimal replacement device for a diseased heart valve, a surgeon generally exerts some level of force to determine a tight fit size. Each surgeon may have a different definition of a tight fit and what is the optimal force that may be exerted. Excessive force can result in inaccurate sizing of the annulus, or even cause tissue damage.

Additionally, a conventional sizer can get entangled in the sub-valvular space of the heart and/or chordae tendineae can become entangled with the external rim of the sizer when the sizer is pushed past the patient's annulus. Disentangling chordae tendineae from the sizer can be time-consuming, delicate and cumbersome. If chordae tendineae are inadvertently withdrawn while the valve sizer is being withdrawn, the mitral structure might collapse.

While the proper sizing determination of a traditional surgical valve may be less sensitive or critical due to the fact that these valves are often parachuted down to the annulus using 12 to 18 sutures which are then used to secure the valve to the annulus, newer valves sometimes employ only three or fewer sutures, which makes sizing accuracy more important. Inaccurate sizing can increase the risks of embolization and paravalvular leaks.

There thus remains a need for an improved heart valve sizer. It is desirable to have a single, one-size-fits-all sizer that could be used to quickly and accurately determine the appropriate valve size for a patient's heart through a minimally sized incision, and which would provide smooth access to the valvular and sub-valvular regions of the heart.

SUMMARY OF THE INVENTION

The embodiments of the present invention have several features, no single one of which is solely responsible for their desirable attributes. Without limiting the scope of the present embodiments as expressed by the claims that follow, their more prominent features will now be discussed briefly. After considering this discussion, and particularly after reading the section entitled "Detailed Description," one will understand how the features of the present embodiments provide advantages over the prior art, which include providing an adjustable force-based heart valve sizer system that can be used to determine the size of a patient's heart valve annulus using a single sizer through a minimally sized incision and providing smooth access to and removal from the valvular and sub-valvular spaces of the heart.

According to the present disclosure, an adjustable valve sizer is provided having a sizer cover configured to deflect and prevent entanglement with chordae tendineae and/or other native heart valve structures. The heart valve sizer comprises a handle, a shaft extending distally from the handle to a distal end, a distal sizing element coupled to the distal end of the shaft, and a sizer cover. The sizing element is preferably size-adjustable between a first, radially-retracted configuration and a second, radially-expanded configuration. The sizer cover has a proximal end and a distal end, the proximal end being associated with the shaft, and the distal end extending distally around at least a portion of the sizing element so as to provide a guard against entanglement of the sizing element with structures of a human heart. The sizer cover is preferably made from an elastomeric material configured to expand and contract in response to conversion of the sizing element between its radially-retracted and radially-expanded configurations. In one embodiment, the distal end of the sizer cover is pleated. In another embodiment, the sizer cover comprises a woven basket made of shape-memory alloy wires configured to expand and contract in response to conversion of the sizing element between its radially-retracted and radially-expanded configurations. A cap can be positioned at a distal end of the woven basket to prevent the woven basket from slipping off the sizing element during use. In some embodiments the sizer cover extends along the length of the sizing element, and completely covers the sizing element. Alternatively, the sizer cover can only partially cover the sizing element.

In another embodiment of the heart valve sizer and cover, the sizing element has a larger diameter than the shaft. The sizer cover has a proximal end and a distal end, the proximal end being attached to the shaft at a location just proximal to the sizing element and the distal end extending distally and widening to a larger diameter around at least a portion of the sizing element so as to provide a conical guard against entanglement of the sizing element with structures of a human heart. The sizing element is size-adjustable between a first, radially-retracted configuration and a second, radially-expanded configuration. A distal portion of the sizer cover is configured to expand and contract in response to conversion of the sizing element between its radially-retracted and radially-expanded configurations. The sizer cover can be made of a generally continuous sheet of material. It can comprise a series of separate elongated elements.

Yet another embodiment is a heart valve sizer cover, comprising a continuous sheet of material configured to surround at least a portion of a sizing element of a heart valve sizer so as to guard against entanglement of the sizing element with structures of a human heart. The sizer cover can be made of a solid elastomeric sheet of material that can, for example, be pleated, or a braided mesh.

In some embodiments, the valve sizer includes a proximal actuator and a shaft extending distally from the actuator. The shaft has a movable member and a stationary member. A sizing element is coupled to the distal end of the shaft. The sizing element can have a hub and a plurality of petals where each petal is radially movable between a first retracted position and a second expanded position. The hub can be fixed to the stationary member in the shaft and the petals can be connected to expand radially upon displacement of the movable member in the shaft. The plurality of petals defines a cylindrical annulus portion and an outwardly extending flange on a proximal end of the cylindrical annulus portion.

The sizer cover at least partially covers the sizing element. The sizer cover can have a generally cylindrical tubular structure, with a proximal end, a canopy, and/or a distal end. The proximal end of the sizer cover is coupled to and wrapped around the outer circumference of the shaft of the valve sizer. The canopy can extend over the hub to the cylindrical annular portion of the sizing element. The distal end of the sizer cover can be coupled to an outer rim of the cylindrical annular portion, at least partially covering the petals. The covered petals can be configured to expand and contract radially upon displacement of the movable member in the shaft.

The sizer cover may be configured in a number of different ways. Illustrative examples include an elastomeric balloon material positioned on the sizer shaft and at least partially covering the sizer petals, a wire mesh basket-like cover structure, a plurality of wires arranged about the circumference of the sizer shaft and sizing element, and/or a plurality of legs arranged about the circumference of the sizer shaft and sizing element. The proximal end of the sizer cover can be fixed with respect to the shaft of the valve sizer or may be movable along the shaft, depending on the configuration. The distal end of the sizer cover may be fixed with respect to the sizing element, such as by being gathered into a cap at the distal end of the sizing petals or secured or coupled to the sizing petals.

In some embodiments, the valve sizer includes a clutch mechanism connected between the actuator and the movable member in the shaft to transmit movement forces between them, wherein movement of the actuator causes displacement of the movable member and consequently outward radial expansion of the petals and/or sizer cover into contact with a surrounding heart valve annulus. The clutch mechanism is configured to slip at a predetermined reaction force imparted by the heart valve annulus against further outward radial expansion of the petals.

The shaft of the valve sizer can include a rod extending through a hollow shaft, and the actuator can include an actuator ring, where the rod may be the stationary member fixed with respect to both the handle and the hub, and the hollow shaft may be fixed with respect to a clutch ring that may be coupled for rotation to the actuator ring via the clutch mechanism. In this configuration, the clutch ring can be connected via a screw thread to the stationary handle so that rotation of the clutch ring causes axial movement of the hollow shaft. The clutch mechanism can include a plurality of bearings biased by springs into detents. The plurality of bearings and the springs can be held within the clutch ring, and the detents can be formed on an inner surface of the actuator ring.

In one version, the plurality of sizer petals, at least partially covered with the sizer cover, moves in a plane substantially perpendicular to a longitudinal axis defined by the shaft of the valve sizer. The movable member moves axially along the shaft and contact and pivot a lever for each of the petals, wherein pivoting of the levers can cause radial expansion of the covered petals. Or, the movable member moves axially along the shaft and connects to a camming member that can directly contact and cause radial expansion of the covered petals. The plurality of petals can define a cylindrical annulus portion and an outwardly-extending flange on a proximal end of the cylindrical annulus portion, and the outwardly-extending flange may have an axially undulating peripheral shape.

In a percutaneous version, the valve sizer is configured for delivery through a catheter and the petals and/or sizer cover are configured to limit the diameter of the sizing element to be small enough to enable passage through the catheter while the petals are positioned in their first retracted position. The petals may remain at least substantially parallel to an axis of the hub while being displaced outward.

These and other features will become apparent with the following description of the embodiments.

BRIEF DESCRIPTION OF THE DRAWINGS

The embodiments of the present disclosure will now be discussed in detail. These embodiments depict the novel and non-obvious features shown in the accompanying drawings, which are for illustrative purposes only. These drawings include the following figures, in which like numerals indicate like parts:

FIGS. 1A-1C each show a perspective view of a covered heart valve sizer with partially covered sizing petals in radially expanded positions, according to the present disclosure;

FIG. 1D shows a perspective view of a covered heart valve sizer with partially covered sizing petals in a radially retracted position;

FIG. 4A shows the sizing element with sizing petals in a semi-expanded position, and FIG. 4B is a cross section thereof;

FIG. 4C shows a petal and a hub assembly from the sizing element of FIG. 4A, while

FIG. 9 shows a perspective view of a heart valve sizer in a radially contracted configuration and having a collar slidably coupled to the sizer shaft;

FIG. 10 shows a perspective view of a heart valve sizer in a radially contracted configuration and having a sizer cover having a plurality of wires and a collar;

DESCRIPTION OF THE PREFERRED EMBODIMENTS

Figure 1A:
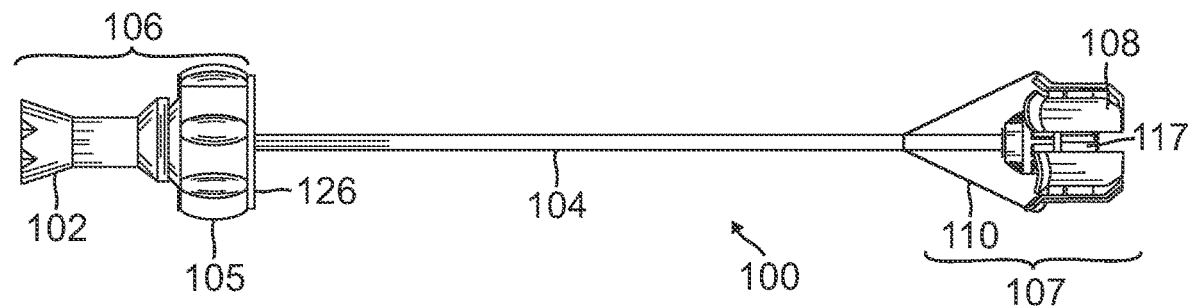
Figure 1B:
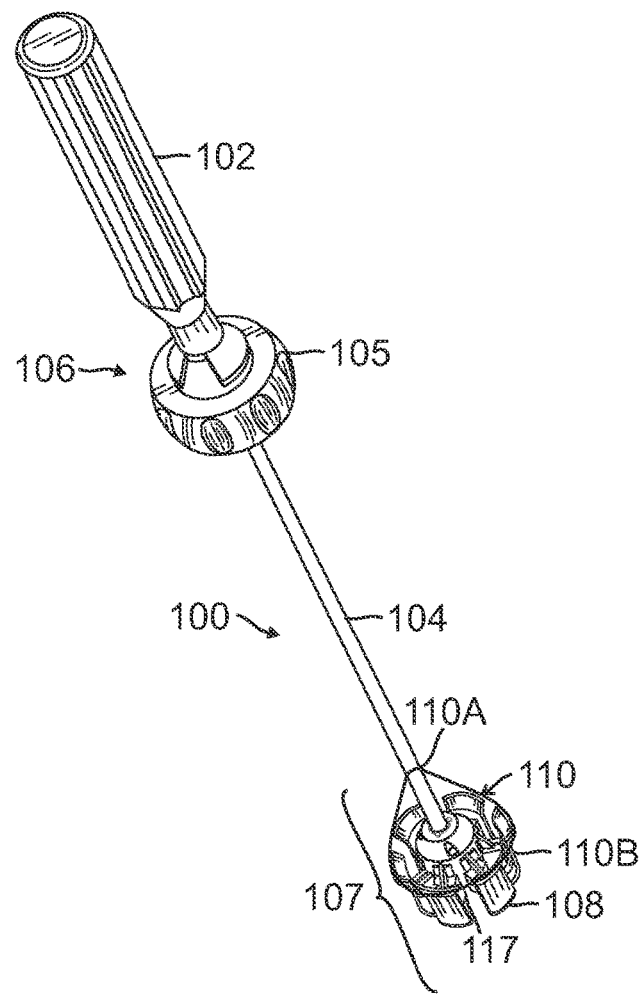
Figure 1E:
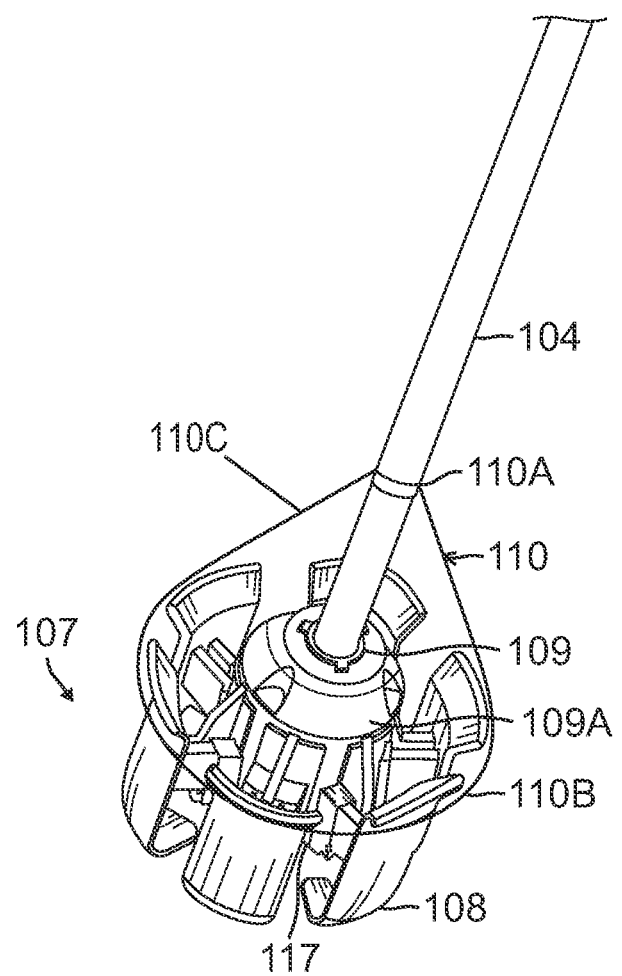
FIG. 1E shows the covered sizing petals in a radially expanded position.

This disclosure describes a covered heart valve sizer that affords improved (e.g., smoother) access to the valvular and sub-valvular spaces of the heart during valve replacement and repair surgeries. The covered valve sizer also provides accurate sizing of the heart valve annulus using a single device rather than requiring the insertion of a series of different sized sizing templates into a patient's native valve. More particularly, sizers that will benefit from covers described herein include both adjustable and non-adjustable sizers.

An exemplary heart valve sizer with a sizer cover is described and/or incorporated in the present disclosure. It is to be understood that the sizer cover may be used with a variety of heart valve sizers to form various examples of a covered heart valve sizer. The sizer cover can be a symmetric sizer cover, such as for heart valve sizers with symmetrical sizing elements. Alternatively, the sizer cover can be an asymmetric sizer, such as for covering heart valve sizers with asymmetric sizing elements. A heart valve sizer cover helps to ensure smooth access to and from the valvular and sub-valvular spaces of the heart.

As used herein, a valve sizer is a "covered" heart valve sizer if the valve sizer has a sizer cover associated with it (e.g., mounted on, coupled to, affixed to, positioned on, or interfaced with), as described herein. Additionally or alternatively, a "covered" heart valve sizer can include heart valve sizers having any type of covering or structure that is configured to guard against entanglement of the valve sizer with structures of a human heart. Sizer covers can include structures such as wires, collars, legs, canopies, mesh structures, elastomeric materials, fabrics, baskets, cages, skirts, umbrellas, shields, and pleated or folded structures. More generally, the cover may be a generally continuous sheet of material, solid or not, or a series of separate elongated elements, as will be clear from the description below. As used herein, a heart valve sizer is "covered" or has a "cover" if it includes some structure configured to guard against, shield from, deflect, and/or prevent entanglement of the valve sizer with structures of the human heart. A heart valve sizer also can be considered to be "covered" if it is shrouded, caged, skirted, shielded, or guarded from structures of the human heart and/or other human anatomy, to improve access to the anatomy.

Generally, examples of a covered valve sizer include a hollow elongated shaft with an actuator assembly at a proximal end of the shaft and a sizing element at the distal end of the shaft. The sizing element includes a hub with a plurality of sizing petals that are configured to extend radially outward from the hub. The valve sizer includes a sizer cover that can be configured to improve performance of the heart valve sizer, and in some examples, may be designed to prevent entanglement of the sizing element with native structures of the patient's heart (e.g., chordae tendineae). The sizer cover may be coupled to the shaft and/or to the sizing elements (e.g., to the sizing petals). In some examples, the sizer cover at least partially covers the sizing element (e.g., at least partially cover the petals of the sizing element). The sizer cover completely covers the sizing element in some examples. Alternatively, the sizer cover may be coupled to the sizing element substantially without covering the sizing element. Various examples of a heart valve sizer having a sizer cover help to ensure smooth entry and exit of the covered sizer from the spaces of the heart. More specifically, the sizer cover can protect the chordae tendineae from entanglement with, for example, the outer rims of the sizing petals. This may prevent time delays and complications or additional processes that might otherwise be necessary to disentangle the chordae tendineae from the sizer during valve replacement or repair surgery.

FIGS. 1A-1E show an illustrative example of a covered heart valve sizer 100. The valve sizer 100 includes an elongated shaft 104 extending along the length of the sizer 100 that may be rigid, flexible, partially rigid, or partially flexible. The shaft 104 may be flexible enough to allow the sizer 100 access to a patient's native valve annulus from different angles, or through curved or bent access passages. An actuator assembly 106 (best seen in FIG. 3A) having an actuator 105 and a clutch cover 126 is coupled to the proximal end of the shaft 104, adjacent a handle 102. A radially expandable sizing element 107 having a sizer cover 110 thereover may be located adjacent the distal end of the shaft 104, opposite the handle 102.

The sizing element 107 preferably includes a hub 117 with a plurality of sizing petals 108 configured to extend radially outward from the hub 117 and to move radially in and out, closer to and away from the hub 117, respectively. As seen in the figures, the sizing petals 108 are arranged around the circumference of the central hub 117. The plurality of sizing petals 108 define a cylindrical annulus portion. The sizer cover 110 desirably at least partially covers the sizing element 107. For example, the sizer cover no at least partially covers the sizing petals 108. In use, the covered sizing petals 108 contract and expand radially while sizing an annulus, without affecting functioning of the petals. Sizing element 107 preferably includes an actuation bearing or hub bearing 109 and a hub cover 109A, the details of which will be explained in further detail below.

As shown in FIGS. 1A-1E, the radially expandable sizing element 107 (e.g., the sizing petals 108 in combination with the hub 117) defines an adjustable outer dimension, such as an outer diameter, of the valve sizing portion at the distal end of the sizer 100 that is radially adjustable through a range of sizes. The outer dimension changes depending on whether the sizing petals 108 are in an expanded position (FIG. 1C), a contracted position (FIG. 1D), or somewhere in between.

Figure 12:
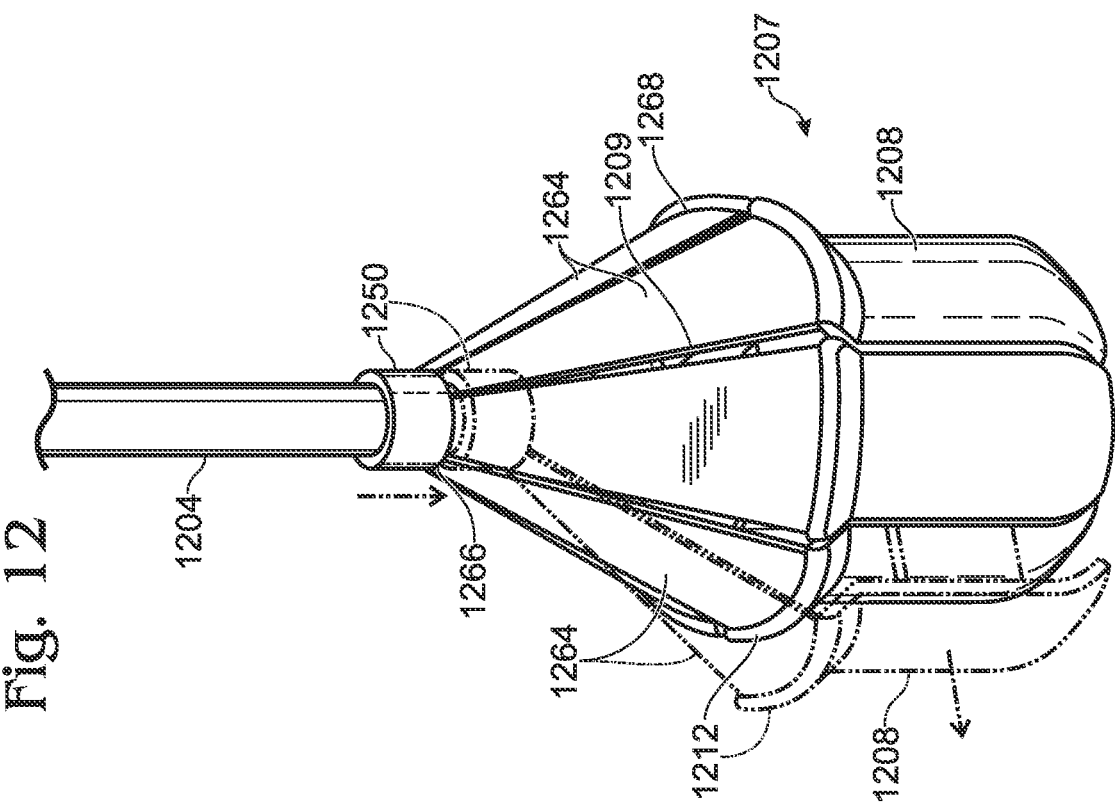
FIG. 12 shows a perspective view of a heart valve sizer in a radially contracted configuration, having fan-shaped legs extending from a collar to sizer petals.
Figure 11:
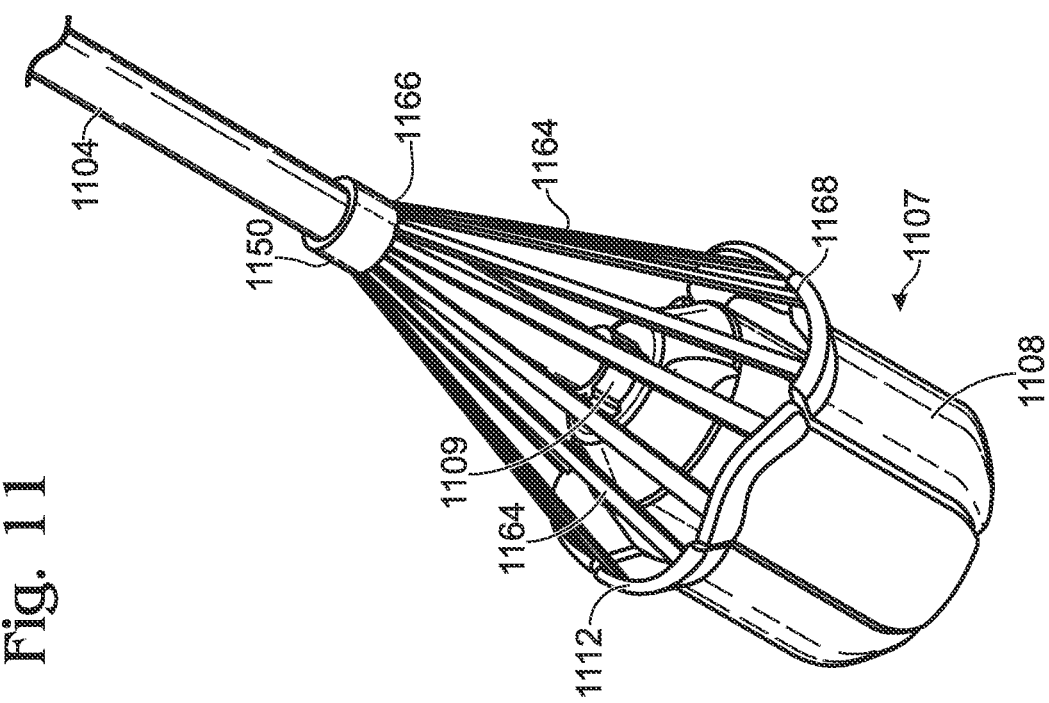
FIG. 11 shows a perspective view of a heart valve sizer in a radially contracted configuration, with a sizer cover having a plurality of legs extending from a collar to sizer petals according to the present disclosure.

The sizer cover 110 is provided over and/or adjacent the sizing element 107. In one example, the sizer cover no is positioned adjacent an exterior surface of the sizing petals 108 such that the petals 108 are positioned between the sizer cover no and the hub 117. In one example, the sizer cover 110 can be an expandable sheath of a generally continuous solid sheet of an elastomeric material such as polyurethane, silicone, polyolefin, any of a variety of hydrogels, or a similar material, such as those that can be used for making medical balloons. Alternatively, sizer covers can be made of a rigid or semi-rigid elastomeric material, and formed such that the cover has pleats resting in the grooves between adjacent petals of the sizing element, as will be explained in more detail below in connection with FIGS. 6A-6C. Sizer covers can include shape memory alloy wires such as Nitinol wires such as in the examples shown in FIGS. 7A-7B and 8A-8B. Sizer covers can also include elongated elements, such as wires or legs, as shown in FIGS. 10-12 and described herein. For example, elongated members, such as wires, can be coupled to the sizing petals and to a movable collar positioned on the shaft, as described in connection with FIGS. 9-10.

Returning now to FIGS. 1A-1E, the material properties of the elastomeric, metallic, polymeric, and/or shape memory materials used with specific examples of sizer covers as described herein allow the sizer cover 110 to remain taut around the sizing petals 108 during various stages of expansion and contraction of the sizing element 107. For example, sizer cover 110 may be made of elastomeric balloon material. As seen in FIG. 1D, the sizer cover 110 can be, for example, a substantially cylindrical tube when the sizing petals 108 are positioned in the radially contracted position. The sizer cover 110 expands to a frusto-conical shape when the covered sizing petals 108 of the valve sizer 100 radially expand, as seen in FIG. 1C.

The sizer cover 110 illustrated in FIGS. 1A-1E preferably includes a proximal end 110A secured to a distal location on the shaft 104, such as with an adhesive or other bond. Alternatively, the proximal end 110A of the sizer cover 110 can be free to move with respect to the shaft 104 (e.g., axially along the shaft 104, towards or away from the proximal end of the shaft 104). A body or canopy 110C (FIG. 1E) of the sizer cover 110 extends in a distal direction from the proximal end 110A and widens radially outward to a size as large or larger than the sizing petals 108. In this regard, the cover 110 forms a conical canopy 110C that forms a tent-like guard against entanglement of the sizing element with structures of a human heart. More specifically, the sizer cover 110 extends from the proximal end 110A over the hub 117 to surround the cylindrical annular portion of the sizing element 107. A distal end 110B of the sizer cover 110 may be fixed to, for example, an outer rim of the cylindrical annular portion of the sizing element 107, at least partially covering the petals 108. For example, the sizer cover 110 can be bonded to one or more of the individual sizing petals 108 using an adhesive. The sizing petals 108 expand and contract radially within the sizer cover 110 upon displacement of a movable member inside the shaft (e.g., the sizer cover 110 is compliant enough so as to expand or contract with the sizing petals 108, and so as to not interfere with or impede radial expansion and contraction of the sizing petals 108), as described herein.

The inner diameter of the proximal end 110A of the sizer cover 110 can be approximately equal to the external diameter of the shaft 104 in some examples. In other examples, the inner diameter of the proximal end 110A of the sizer cover 110 can be slightly smaller than the external diameter of the shaft 104 so as to provide a friction fit between the proximal end 110A of the sizer cover 110 and the shaft 104. In still other examples, the inner diameter of the proximal end 110A of the sizer cover 110 can be slightly larger than the external diameter of the shaft 104 so as to allow freedom of movement of the proximal end 110A along the shaft 104.

The inner diameter of the distal end 110B of the sizer cover no can conform to the external circumference of the sizing element 107 (e.g., the inner diameter of the distal end 110B of the sizer cover 110 is defined by the outer diameter of the sizing petals 108). The sizer cover no expands from a first, smaller diameter conforming to the retracted position of the sizing petals 108 of the sizing element 107 (FIG. 1D), to a second, larger diameter conforming to the expanded position of the sizing petals 108 (FIG. 1C). The expansion and contraction of the covered sizing petals 108 is controlled by the actuator assembly 106. As can be seen, the sizer cover no can be positioned to cover at least the proximal edges of the sizing petals 108, thereby providing smooth access to and from the valvular and sub-valvular spaces of the heart during a valve sizing procedure.

Figure 2A:
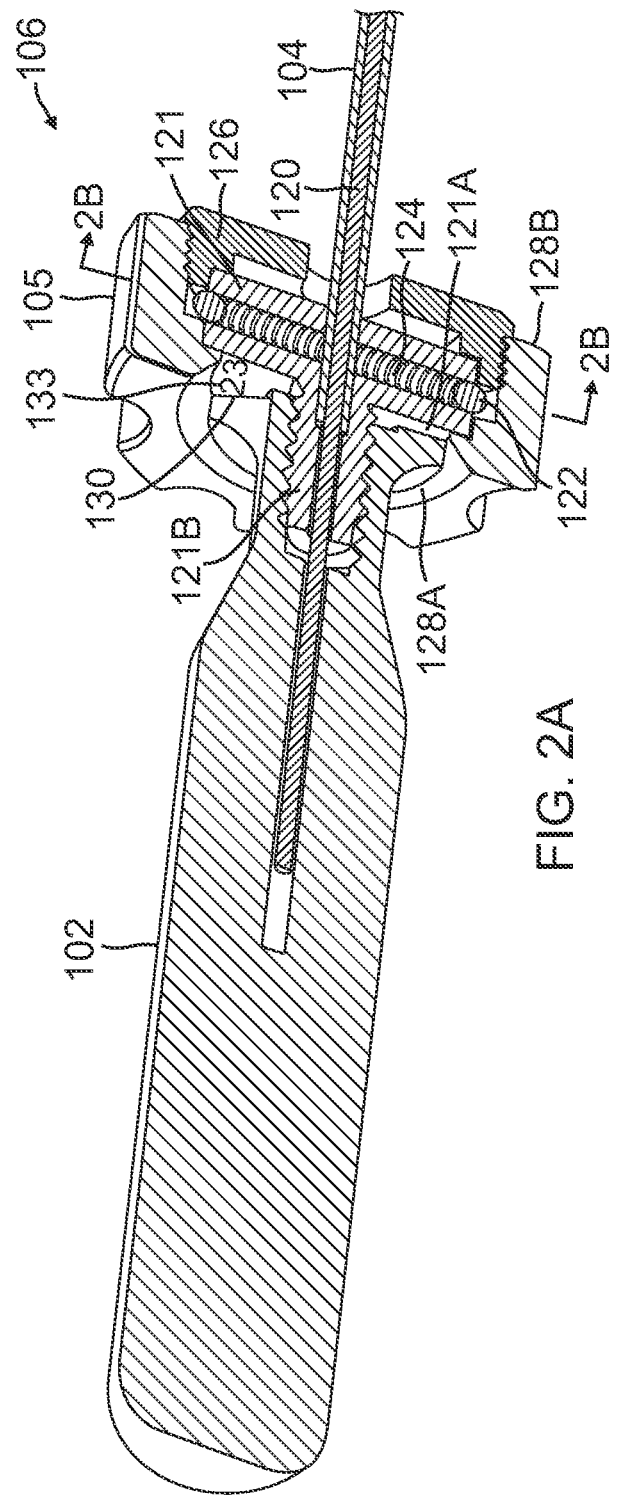
FIGS. 2A-2C show cross-sectional views of an actuator assembly for the various sizing elements disclosed herein.
Figure 2B:
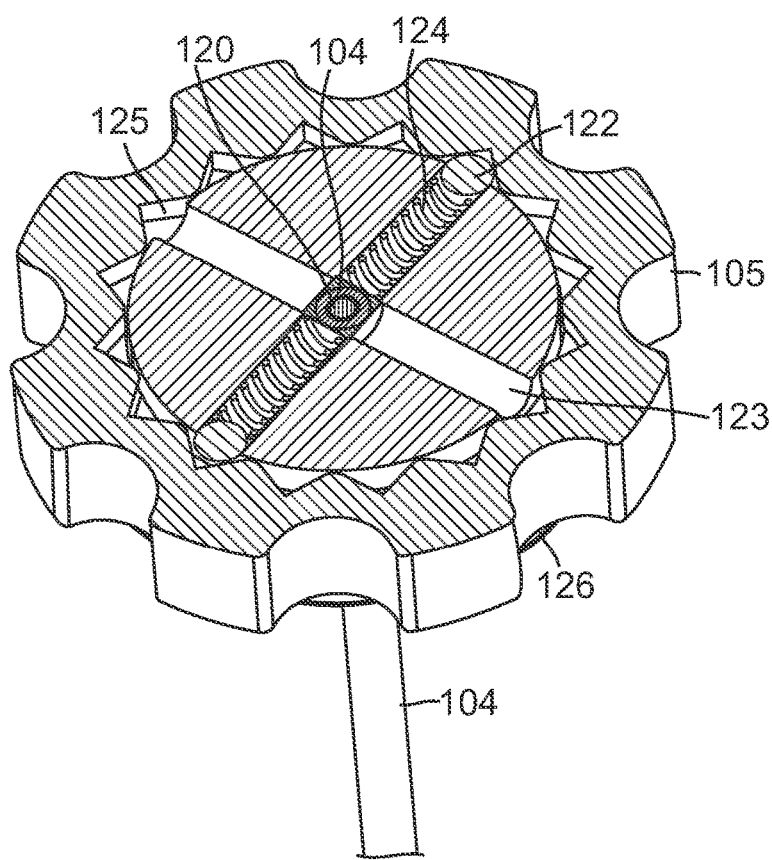
Figure 2C:
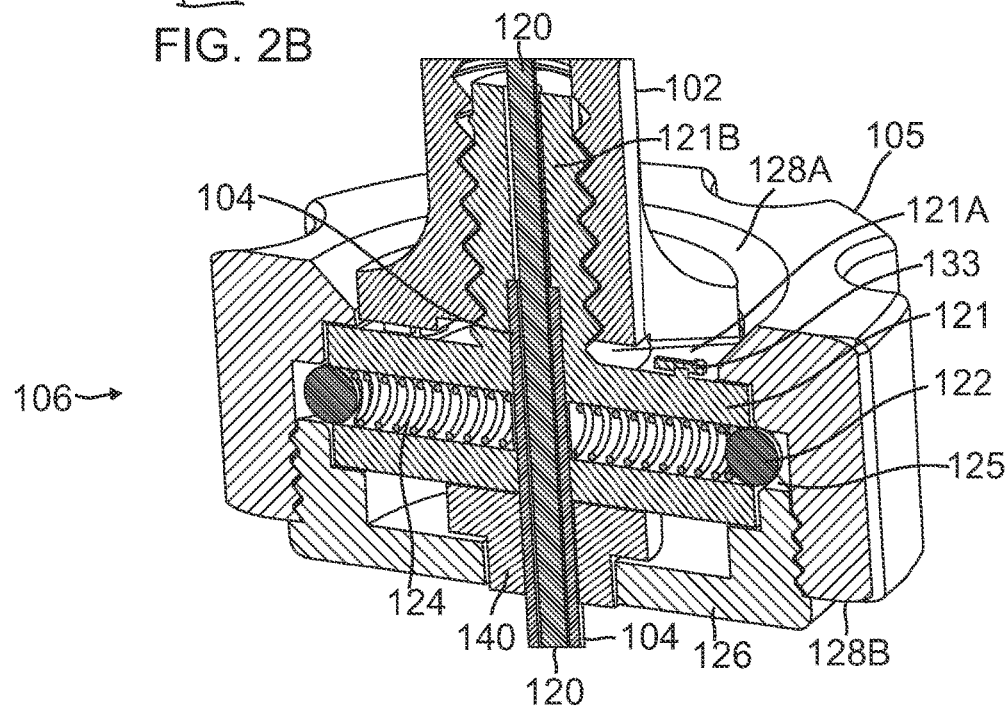

FIGS. 2A-2C show components of the actuator assembly 106 of the valve sizer 100 of FIGS. 1A-1E. The actuator assembly 106 can include an actuator 105, a handle 102, a clutch ring 121, and a clutch cover 126 mounted inside the actuator 105. The handle 102 may be fixed with respect to the shaft 104 and may be used for keeping the valve sizer 100 steady in the hands of the operator. The handle 102 can engage a tubular threaded portion 121B that extends axially up from the clutch ring 121 towards the proximal end of the shaft 104. The clutch ring 121, in turn, is mounted to the shaft 104. Rotation of the clutch ring 121 relative to the handle 102 causes axial displacement of the clutch ring 121 relative to the handle 102. The handle 102 can be used for positioning the radially expandable sizing element 107 (FIGS. 1A-1E) at the distal end of the shaft 104 inside a patient's native valve annulus. The act of rotating the actuator 105 and the clutch ring 121 causes expansion and retraction of the radially expandable sizing element 107, depending on the direction of rotation, until the size of the valve sizing portion (e.g., the sizing petals 108 of FIGS. 1A-1E) corresponds to the size of the native valve annulus being sized. Once the operator determines that the sizing petals 108 are radially expanded to the size of the native valve annulus, the sizer 100 provides information as to the appropriate size of replacement valve to use for the particular patient. In this way, a single, adjustable sizer 100 can be used to determine which of a variety of replacement valve sizes is appropriate for a given patient.

Various actuators, actuation assemblies and clutch mechanisms for heart valve sizers are described in co-pending U.S. Patent Publication No. 2013/0150954, filed Dec. 6, 2012, entitled "Force Based Heart Valve Sizer," and assigned to the assignee of the present application, the full disclosure of which is hereby incorporated herein by reference.

FIGS. 2A-2C provide cross-sectional views of the actuator assembly 106. In a particular example, the distal end of the handle 102 includes a window 130 that allows for visibility of a sequence of numerical markings 133 on the clutch ring 121 (such as on a surface of a cylindrical base 121A), where the numerical markings 133 are configured to indicate the current size of the expandable sizing element at the distal end of the valve sizer 100. For example, as the sizing petals 108 are radially expanded, the clutch ring 121 is rotated, and a different numerical marking 133 is visible in the window 130 depending on the extent of the radial expansion of the sizing petals 108. Thus, a different numerical marking 133 is visible for each incremental expansion of the sizing petals 108, and the numerical markings 133 indicate the appropriate replacement valve size to use by looking at the visible numerical marking 133 when the sizing petals 108 are expanded to the size of a particular patient's native valve annulus.

The clutch ring 121 may have a tubular threaded portion 121B extending laterally into the handle 102. Rotation of the actuator 105 causes rotation of the clutch ring 121 and the markings 133 on it past the window 130 until a predetermined torque limit is reached, at which point a clutch mechanism is configured to slip so that further rotation of the actuator 105 is decoupled from the clutch ring 121, at which point the valve size corresponding to the torque limit is displayed in the window 130. The actuator 105 may continue to expand the sizing element 107 outwardly until the sizing petals 108 contact the surrounding native valve annulus, at which point the resistance imparted to the sizing element 107 transmits back through the clutch mechanism, which decouples rotation of the actuator 105 from the clutch ring 121. In this manner, once the actuator 105 has become decoupled from the clutch ring 121, further rotation of the actuator 105 will no longer further expand the sizing petals 108, thereby preventing the sizing petals from exerting too much pressure against the patient's native valve annulus.

The actuator 105 can include a top recess 128A and a bottom recess 128B. In some examples, the handle 102 engages at least a portion of the tubular threaded portion 121B of the clutch ring 121 inside or within the actuator top recess 128A. The clutch ring 121 is fixed with respect to the hollow shaft 104, with the handle 102 attached to a fixed length cable or rod 120 that extends through the shaft 104. The length of the cable or rod 120 that extends between the hub 117 (FIGS. 1A-1E) and the handle 102 is fixed so that the rod 120 forms a stationary member between the handle 102 and the hub 117.

FIG. 2B shows the ratchet mechanism for the clutch ring 121 according to one example. Generally, the shaft 104 can be coupled to a mechanism that expands the sizer 100 and is coupled to the clutch actuator 105 by a ratcheting mechanism. A cylindrical base 121A of the ring 121 includes one or more springs 124 inserted into or extending across at least one diametric hole 123. Spring-loaded bearings 122 are seated into a series of cutouts or detents 125 formed on an inner surface of the surrounding actuator ring 105. Rotation of the actuator ring 105 thus causes rotation of the clutch ring 121 until the bearings 122 slip from the detents 125 against the force of the springs 124.

The clutch ring 121 and the actuator 105 function as a ratcheting mechanism such that when a predetermined amount of torque is applied, the actuator 105 ratchets and does not drive the shaft 104 any further. Therefore, the size of the native valve annulus is determined by rotating the actuator 105 until the clutch ring 121 begins to ratchet. The actuator 105 is coupled to the clutch ring 121 such that the rotation of the actuator 105 causes the shaft 104 to move. The force needed to overcome the ratchet mechanism may be set to correspond to the reaction force being applied to the sizing petals 108 by the annulus being sized. That is, the reaction force imparted by the annulus to the sizer wo as the sizing petals 108 expand may be configured to gradually increase until the sizing petals 108 fully engage the native valve annulus. The reaction force creates a reaction torque in the shaft 104 which eventually overcomes the springs 124 in the ratchet mechanism such that the clutch ring 121 slips. The numerical markings 133 can indicate an outer diameter of the native valve annulus and/or the numerical markings 133 may indicate the appropriate size of replacement valve to use for a particular patient. The torque at which the clutch ring 121 slips can be calibrated to match a particular reaction force experienced by the sizing element 107, such as by varying the spring force and/or the number or character of the bearings 122, springs 124, and/or detents 125.

As seen in FIG. 2C, a stepped washer 140 can be positioned to abut the lower end of the clutch ring 121 towards the bottom recess 128B of the actuator 105. The stepped washer 140 is mounted in place on the shaft 104, such as with an adhesive. A clutch cover 126 is positioned to snap fit over the clutch ring 121, and can be in threaded engagement within the actuator 105. The clutch cover 126 may thereby be configured to lock the stepped washer 140 and the clutch ring 121 in place within the actuator 105 adjacent the bottom recess 128B. The stepped washer 140 can be captured between the clutch cover 126 and the lower surface of the clutch ring 121. Along with the shaft 104, the stepped washer 140 moves distally and proximally along the rod 120 with activation of the actuator mechanism.

Figure 2D:
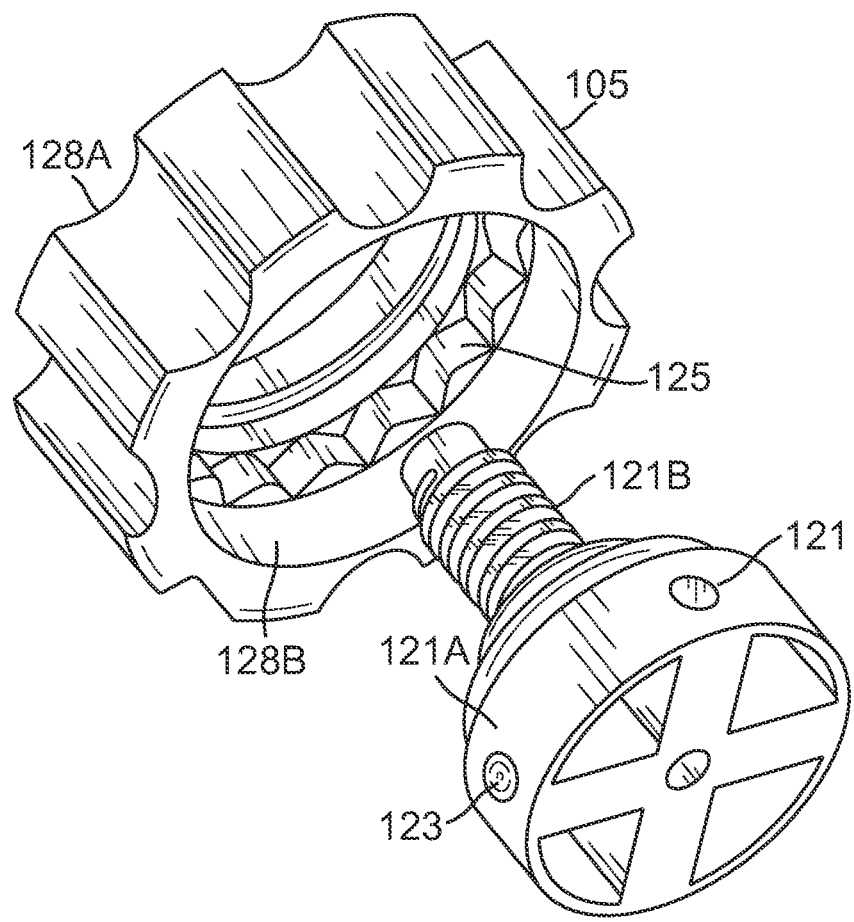
FIG. 2D shows an exploded view of an actuator assembly including an actuator ring and a clutch ring.

FIG. 2D is an exploded view of the actuator 105 and the clutch ring 121. Clutch ring 121 is inserted through the actuator 105 so that the tubular threaded section 121B extends through the center of the actuator 105 and its top recess 128A.

Although examples have been described using the rotating actuator 105 to move the covered sizing petals 108, any other actuation mechanism can be used including a trigger, sliding lever, and/or scissors-type actuator assembly 106. The hollow shaft 104 can form a movable member between the handle 102 and hub 117, and transmit the force needed to operate the sizing petals 108. Other movable members are possible, and the movement need not be linear but could alternatively or additionally be rotational. Essentially, there is typically a stationary member (e.g., rod 120) that holds the hub 117 from moving relative to the handle 102, and a movable member (e.g., the shaft 104) that transmits the driving force from the handle to the hub 117 to operate the covered sizing petals 108, and a variety of such mechanisms are within the scope of the present disclosure.

The ball-spring-detent type of clutch mechanism may advantageously provide relatively low sensitivity to environmental factors. Thus, in some examples, the accuracy of the torque limit is known with a high degree of accuracy and is not significantly affected by temperature or fluids (e.g., blood). Repeatable results in the operating room make such a clutch system advantageous over one which relies on frictional forces, as the coefficient of friction of the contact surfaces can change when subjected to a wet environment, temperature fluctuations, and/or after being sterilized.

Figure 3A:
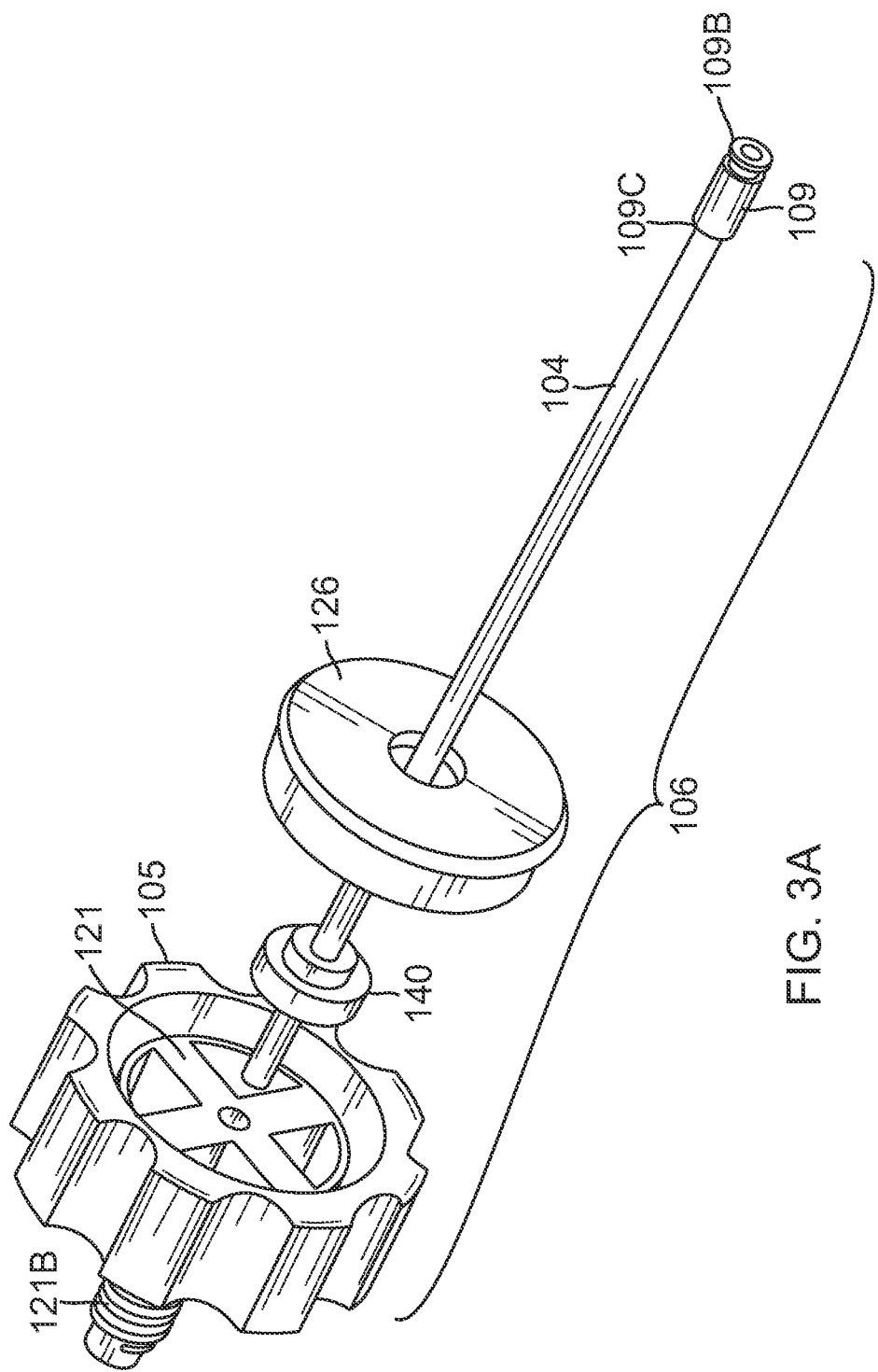
FIGS. 3A and 3B show an actuator assembly exploded and assembled with a sizing element having a hub cover.

FIG. 3A shows the actuator assembly 106 mounted on the shaft 104, which terminates in an actuation bearing or hub bearing 109. As shown in FIG. 3A, the clutch ring 121 is positioned within the actuator 105. The clutch cover 126 engages with an inner surface of the actuator 105 (e.g., external threads on the clutch cover 126 (not shown in FIG. 3A) engage with internal threads in the actuator 105 (not shown in FIG. 3A) to lock the stepped washer 140 and clutch ring 121 in place within the actuator 105). Actuator bearing 109 is positioned adjacent a distal end of the shaft 104.

Figure 3B:
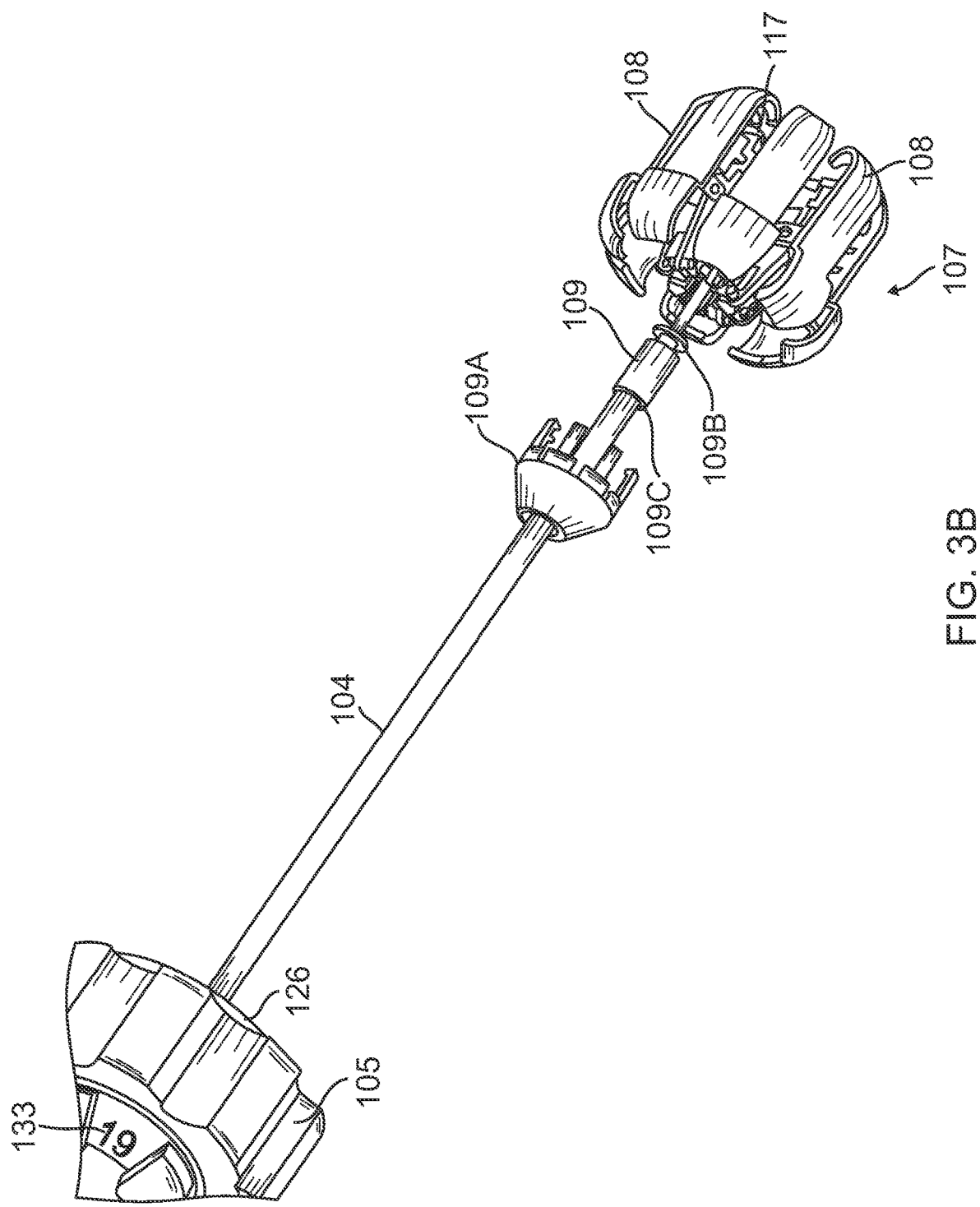

FIG. 3B shows the shaft 104 and actuation bearing 109 positioned just proximal to the sizing element 107. In some examples, axial displacement of the actuation bearing 109 within the sizing element 107 can cause radial movement of the sizing petals 108, such as via a camming and linkage system, as described in more detail in connection with FIGS. 4A-4D.

Figure 4C:
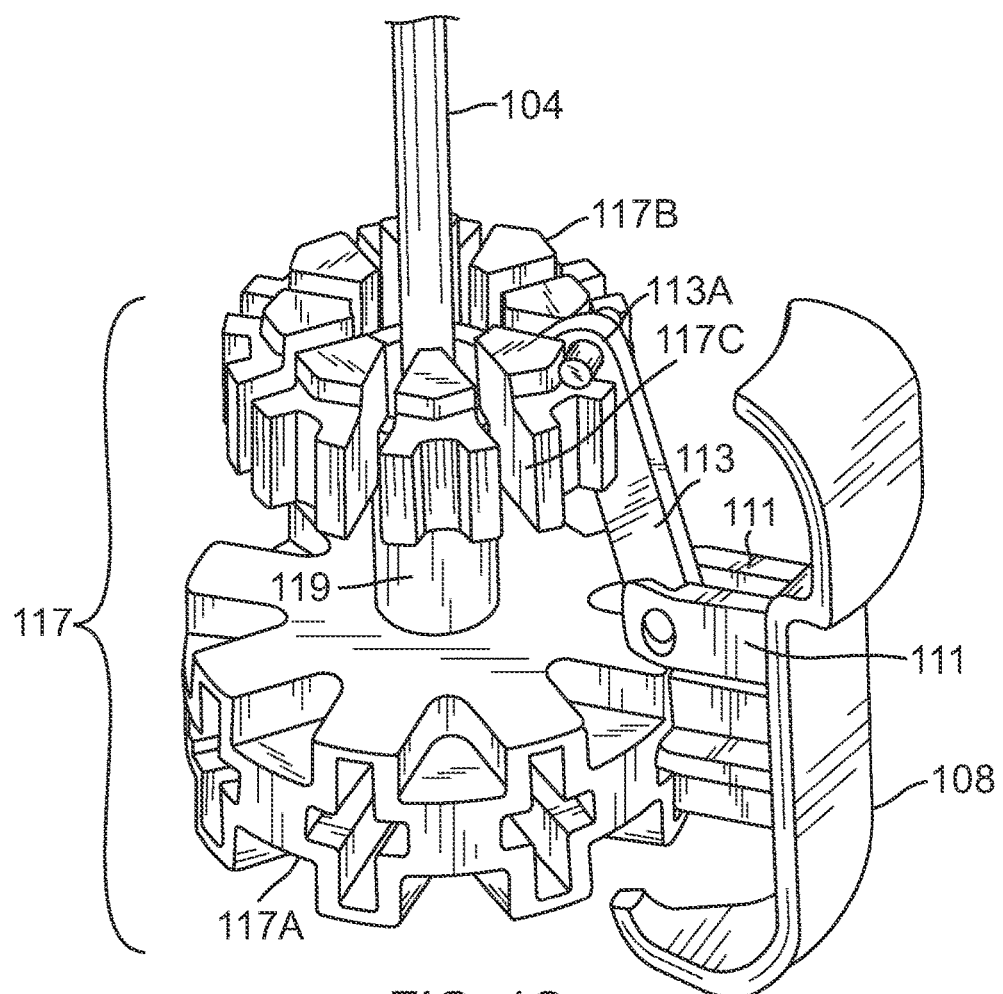

As seen in FIGS. 4A and 4B, the actuation bearing 109 can include a distal end 109B and a proximal end 109C. The hub cover 109A rests over or around the proximal end 109C of the actuation bearing 109. As shown in the figures, the distal end 109B of the actuation bearing 109 is shaped like a disc. FIGS. 4B and 4C show that the hub 117 includes a top hub portion 117B and a bottom hub portion 117A connected through a shaft stub 119, which extends through the center of the top hub portion 117B to the bottom hub portion 117A of the hub 117. A fixed length cable or rod 120 extends into and is fastened within the shaft stub 119, and thereby extend into and be fastened within the hub 117. In this way, the distance between the handle 102 and hub 117 remains constant. The top portion 117B and the bottom portion 117A can include a plurality of features, such as slots 117C in the top portion 117B, splaying outward around a central axis. The slots 117C can be configured to interact with linkages 113 (also referred to herein as levers 113) to move the sizing petals 108 radially inward and outward. Such interactions form a camming assembly or mechanism which can be configured to radially expand or contract the sizing petals in response to rotation of the actuator 105.

Figure 4D:
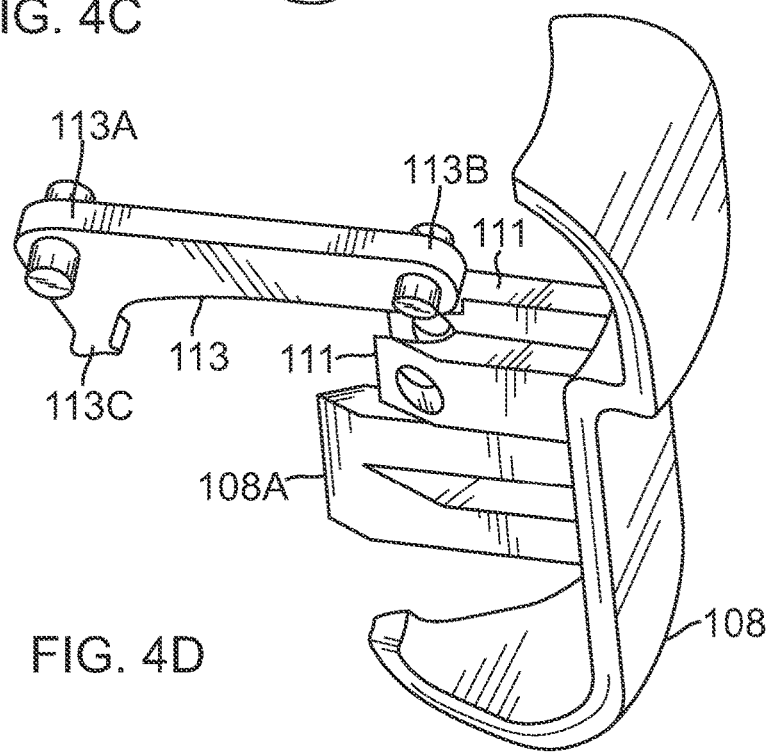
FIG. 4D shows a single petal and a lever that links the petal to the hub.

The camming assembly can include a plurality of levers 113 for coupling the petals 108 with the hub 117, shown for one petal in FIGS. 4C-4D. The number of levers 113 preferably corresponds to the number of petals 108 (e.g., the sizing element 107 includes one lever 113 for each sizing petal 108). Each proximal end 113A of each respective tapered lever 113 extends through a corresponding respective slot 117C of the hub 117. As seen in FIG. 4B, a finger 113C of each lever 113 extends into an annular groove 109D between the distal end 109B and proximal end 109C of the actuation bearing 109.

An outer end 113B (also referred to herein as distal end 11B in some positions) of each lever 113 can be connected, such as via a journal pin, to a bifurcated pair of inwardly-extending arms 111 on each sizing petal 108. For example, the distal end 113B of each respective lever 113 can be coupled to a respective pair of inwardly-extending arms 111 on each respective sizing petal 108. Rotation of the actuator 105 ultimately leads to axial movement of the shaft 104 and actuation bearing 109. Axial movement of the actuation bearing 109 causes movement of the levers 113 by virtue of the camming interaction between the annular groove 109D and each lever finger 113C. The distal end 113B of each lever 113 is configured to pivot outwardly in reaction to distal movement by the actuation bearing 109, thereby causing radial expansion of the petals 108. Similarly, the distal end 113B of each lever 113 is configured to pivot inwardly in reaction to proximal movement of the shaft 104 and actuation bearing 109, which may thereby retract the petals 108 radially inward, thereby reducing the profile of the sizing element 107 to facilitate removal from the native annulus after a sizing procedure.

The camming assembly can further include a hub cover 109A that snap fits to the hub 117, and the actuation bearing 109 can extend through the hub cover 109A to fit within a bore in the top portion of the hub 117B. Actuation bearing 109 can be coaxially placed around and fastened to the hollow shaft 104 and aligned with the shaft stub 119 of the hub 117. Both the hollow shaft 104 and actuation bearing 109 can be configured to slide over the rod 120, which can be anchored in the hub 117. Displacement of the hollow shaft 104 can thus displace the actuation bearing 109 relative to the hub 117.

Figure 5A:
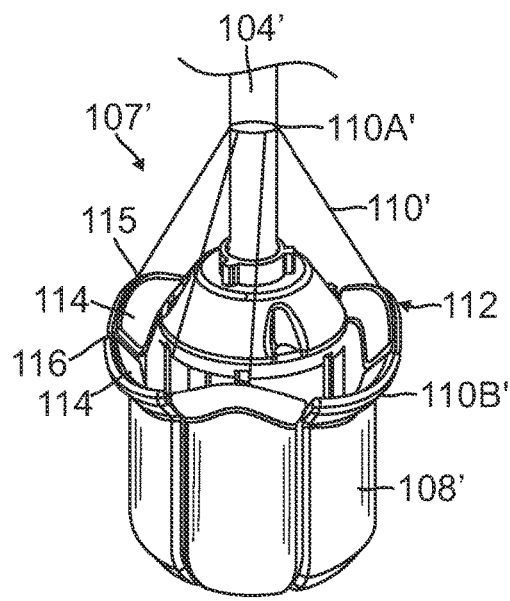
FIG. 5A shows a sizing element with the sizer cover partially covering the external rim of the sizing petals.
Figure 5B:
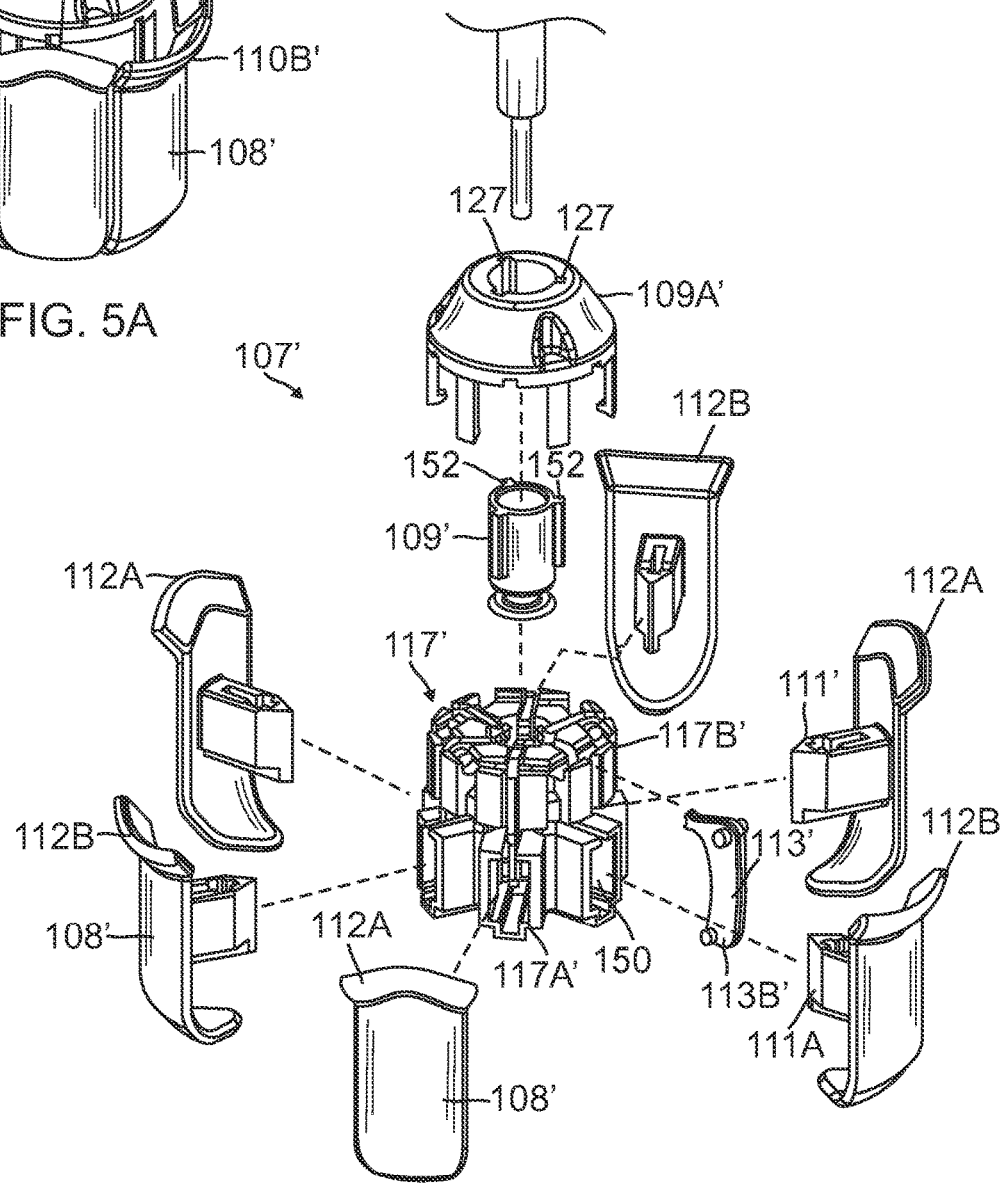
FIG. 5B shows an exploded view of an alternative sizing element of the present application.

FIGS. 5A-5B illustrate a modified sizing element 107' much like the previously-described sizing element 107, with like parts' numbers having a prime designation. The sizing element 107' preferably includes a plurality of sizing petals 108' covered at least partially by a sizer cover 110'. The sizing petals 108' contract about a hub 117' into a first, reduced diameter configuration seen in FIG. 5A. Each of the sizing petals 108' have a proximal flange 114 that in aggregate define an undulating or scalloped peripheral flange 112 that extends slightly outward from the main cylindrical body of the sizing element 107'. More particularly, each sizing petal 108' may have either a convex (undulating in) flange 112A or a concave (undulating out) flange 112B, as seen best in the exploded view of FIG. 5B. In some examples, and as seen in FIG. 5B, the type of proximal flange 114 can alternate from one adjacent sizing petal 108' to the next, such that each sizing petal 108' having a convex flange 112A may be positioned between a pair of sizing petals 108' having a concave flange 112B.

In a specific example, a sizing element 107' includes six sizing petals 108' with three sizing petals 108' having convex flanges 112A and three sizing petals 108' having concave flanges 112B. The aggregate flange 112 thus defines an undulating peripheral shape with three peaks 115 and three valleys 116 (FIG. 5A), thereby mimicking the natural contours of an aortic annulus and the shape of the sewing ring of a prosthetic heart valve, where the peaks 115 are configured to correspond to the commissures of a prosthetic heart valve and the valleys 116 are configured to correspond to the cusps in between the commissures of the prosthetic heart valve. This scalloped peripheral flange 112 facilitates proper seating of the sizing element 107' down into the aortic annulus so that the substantially cylindrical body formed by the petals 108' extends fully within a patient's native valve annulus so that the sizer more accurately reflects the size of the native annulus orifice.

The sizer cover 110' preferably covers at least a portion of the sizing element 107'. A proximal end 110A' of the sizer cover 110' can be disposed on a shaft 104', and a distal end 110B' of the sizer cover 110' can be affixed to the outer rim of the annular portion of the sizing element (e.g., the distal end 110B' of the sizer cover 110' is coupled to the peripheral flange 112 of the sizing element 107').

In some examples, each of the petals 108' have inwardly-extending arms 111' that include pointed inner ends 111A that facilitate assembly with the distal ends 113B' of the levers 113'. The pointed inner ends 111A also facilitate coupling of the sizing petals 108' to the receiving channels 150 formed in the bottom portion 117A' of the hub 117'. The pointed inner ends 111A also provide maximum overlap between the internal radial channels 150 in the hub 117' and the sizing petals 108', which facilitates full expansion of the sizing element 107' for larger annuluses (e.g., at least around 29 mm, in some examples). Additionally or alternatively, the actuation bearing 109' can include one or more axial ribs 152 that can be configured to mate with a respective axial groove 127 in the hub cover 109A' to at least substantially prevent relative rotation between the hub cover 109A' and the actuation bearing 109'. The sizing element 107' functions in essentially the same way as the previously-described sizing element 107, and thus will not be further described.

Any of the various examples of a heart valve sizer having a sizing element with radially expanding sizing petals as described and/or incorporated herein can be provided with a sizer cover, where the sizer cover is positioned such that it at least partially covers, overlaps, and/or engages with one or more of the sizing petals. Moreover, certain stationary, fixed, or non-adjustable heart valve sizers may benefit from the covers disclosed herein, especially those with relatively complex outer shapes (as opposed to simple cylinders, for example). In some examples, the sizer cover helps prevent entanglement of the sizing petals with a patient's anatomy, such as with the chordae tendineae. The sizer cover provides a smoother interface for the exterior surface of the sizing element, and thereby facilitates insertion, expansion, and removal of the sizing element once retracted. Various examples of a sizer cover and their variations will now be described with reference to the following figures. Any of the examples of sizer covers described herein may be used in combination with any of the herein-described and/or herein-incorporated heart valve sizers or sizing elements or any of their variations.

Figure 6A:
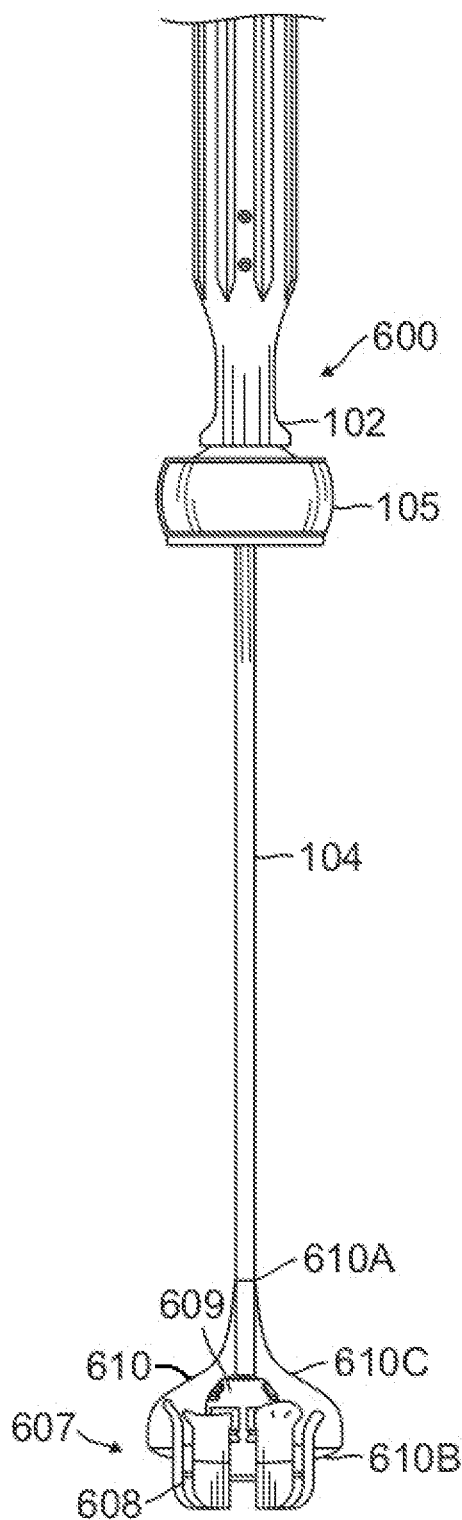
FIGS. 6A-6C show the heart valve sizer with a rigid sizer cover, according to one example.
Figure 6B:
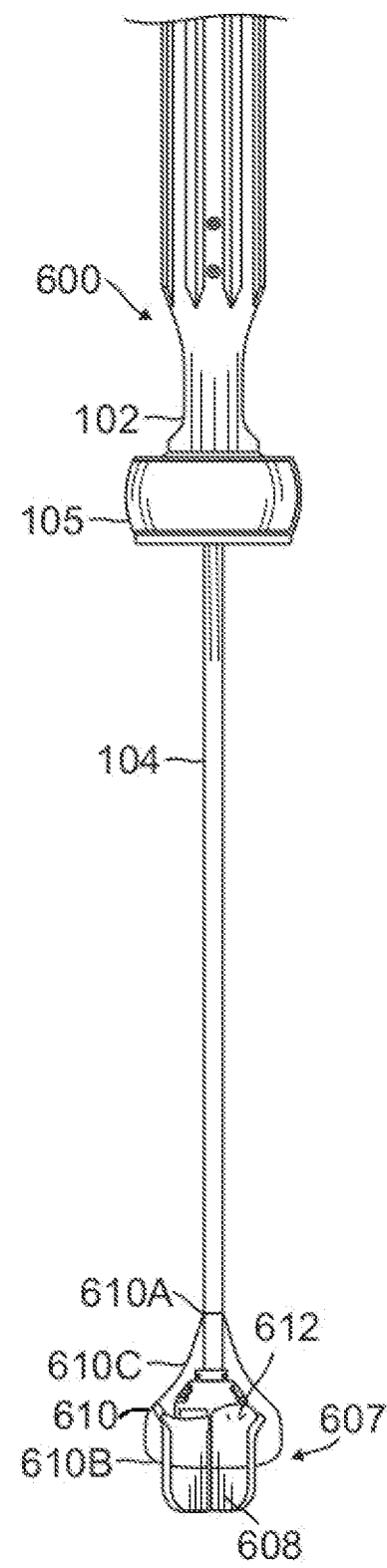
Figure 6C:
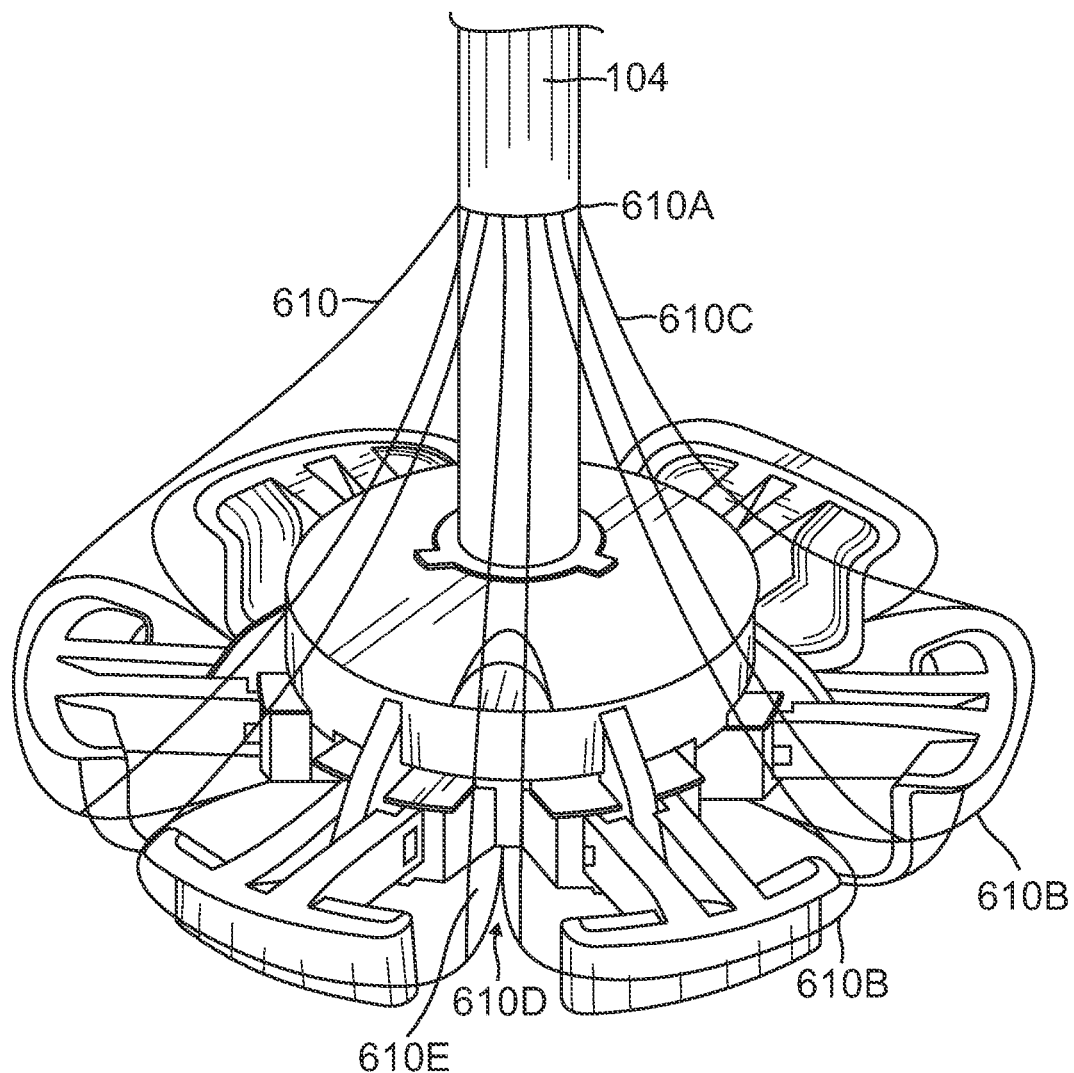

One example of a sizer cover 610 is an elastomeric balloon made of, for example, extruded tubing, as shown in connection with the heart valve sizer 600 shown in FIGS. 6A-6C. A proximal end 610A of the sizer cover 610 is fixed around the distal end of the sizer shaft 104, with a canopy 610C extending over the hub cover 609. A distal end 610B of the sizer cover 610 preferably covers and/or overlaps at least a portion of the sizing petals 608. In some examples, the sizer cover 610 is fixed to the outer rim of the annular portion of the sizing element 607. In some examples, the distal end 610B of the sizer cover 610 is coupled to the sizing petals 608, such as with an adhesive, sutures, and/or any other suitable fastening means. In some examples, the distal end 610B of the sizer cover 610 is coupled to a peripheral flange 612 formed by the proximal edges of the sizing petals 608.

In some examples, and as shown in FIG. 6C, the distal end 610B of the sizer cover 610 is pleated such that folds 610E are formed within grooves 610D between the adjacent petals 608 of the sizing element 607 when the covered petals 608 are retracted. Although pleated, the sizer cover 610 retains its form as a generally continuous sheet of material. When the sizing petals 608 expand radially outward from the shaft 104, the pleated sections 610E of the semi-rigid cover 610 unfold or stretch out and allow expansion of the sizer cover 610. Thus the outer diameter of the distal end 610B of the sizer cover 610 may change, for example, from about 23 mm in a fully contracted position (FIG. 6B) to about 33 mm in a fully expanded position (FIG. 6A), while the diameter of the canopy 610C of the sizer cover 610 diameter may change, for example, from about 19 mm in a fully contracted position to about 29 mm in a fully expanded position.

Figure 7A:
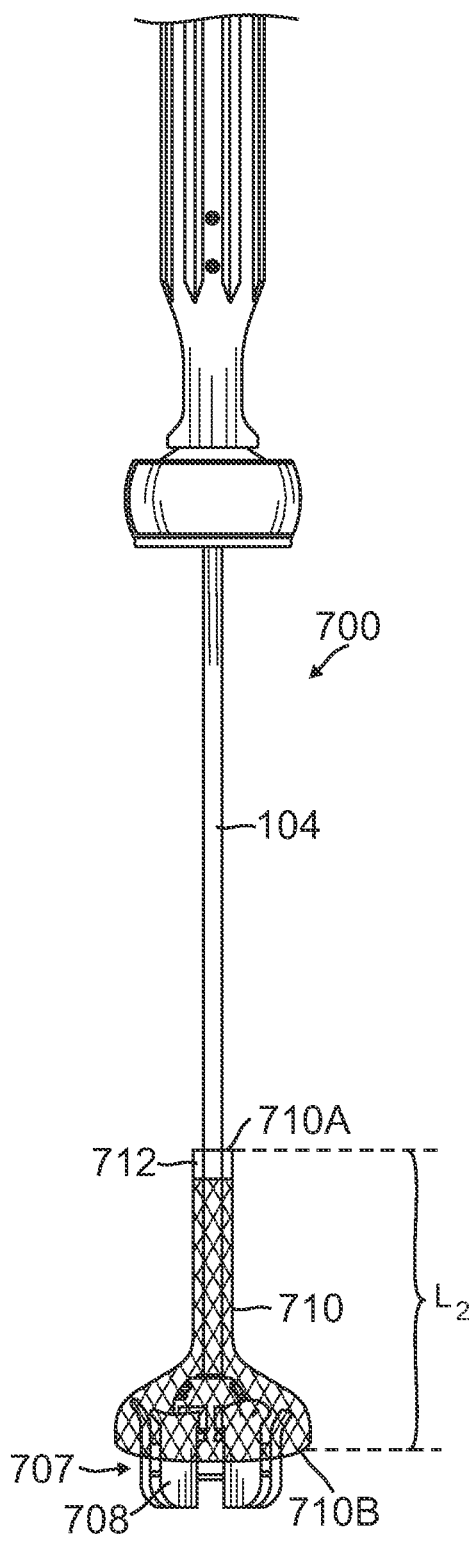
FIGS. 7A-7B show the heart valve sizer with a basket-like cover partially covering the sizing element, according to another example.
Figure 7B:
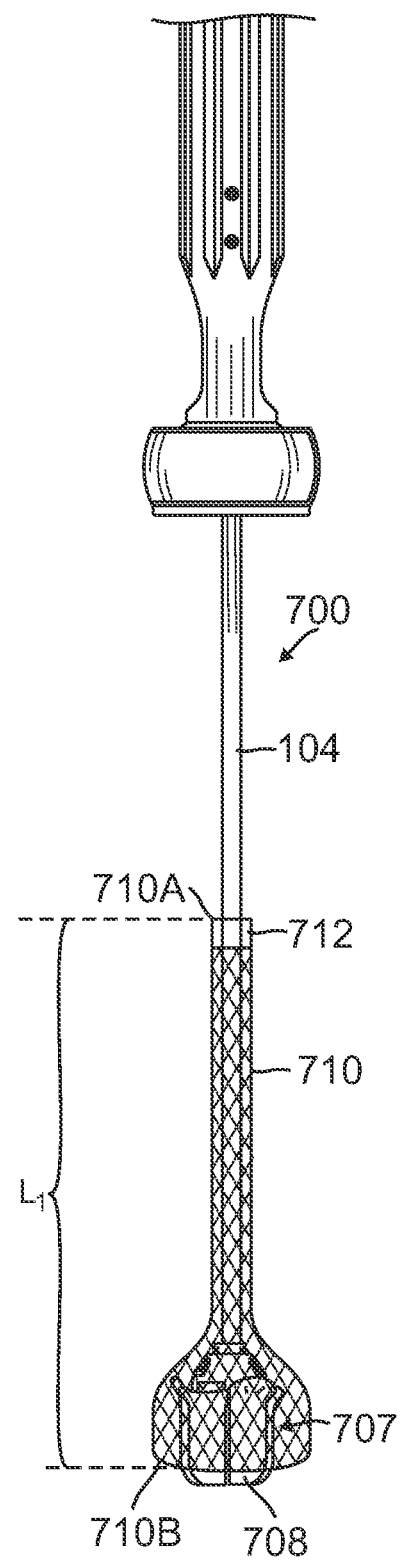

FIGS. 7A-7B show yet another example of a valve sizer 700 having a sizer cover 710 according to the present disclosure. The sizer cover 710 of the valve sizer 700 can be made of, for example, stainless steel and/or shape memory alloy wires, such as Nitinol wires. The wires can be braided or woven together to form a mesh, basket-like sizer cover 710 that at least partially covers, overlaps, and/or envelops the sizing element 707. The braided cover 710 defines a generally continuous sheet of material, albeit with pores or holes in the braid. A proximal end 710A of the sizer cover 710 surrounds the shaft 104, such as by way of a collar 712 that is configured to slide freely up and down on the shaft 104. The distal end 710B of the sizer cover 710 can be associated with the outer rim of the annular portion of the sizing element 707, such as in a manner so as to be flexible to allow the sizer cover 710 to move in response to the radial expansion and contraction of the sizing petals 708. In some examples, the distal end 710B of the sizer cover 710 can be sutured to the individual petals 708 (or to a fabric cover on the sizing petals 708) of the sizing element 707. Alternatively or additionally, the distal end 710B of the sizer cover 710 can be attached to the sizing petals 708 using adhesives. The basket-like sizer cover 710 can be rigid enough to hold its shape such that it remains at the distal end of the sizer 700 without any attachment at all in some examples. In some examples, as the sizing element 707 expands radially outward, the basket of wires (e.g., the sizer cover 710) shortens from an initial length of $L_1$ (FIG. 7B) corresponding to a contracted sizing element 707 to a second, shorter length of $L_2$ (FIG. 7A) corresponding to an expanded sizing element 707. This "foreshortening" is a well-known phenomenon with braided tubes whose individual strands are connected and thus when one or more are radially expanded they pull on the rest, thereby shortening the entire length.

Figure 8A:
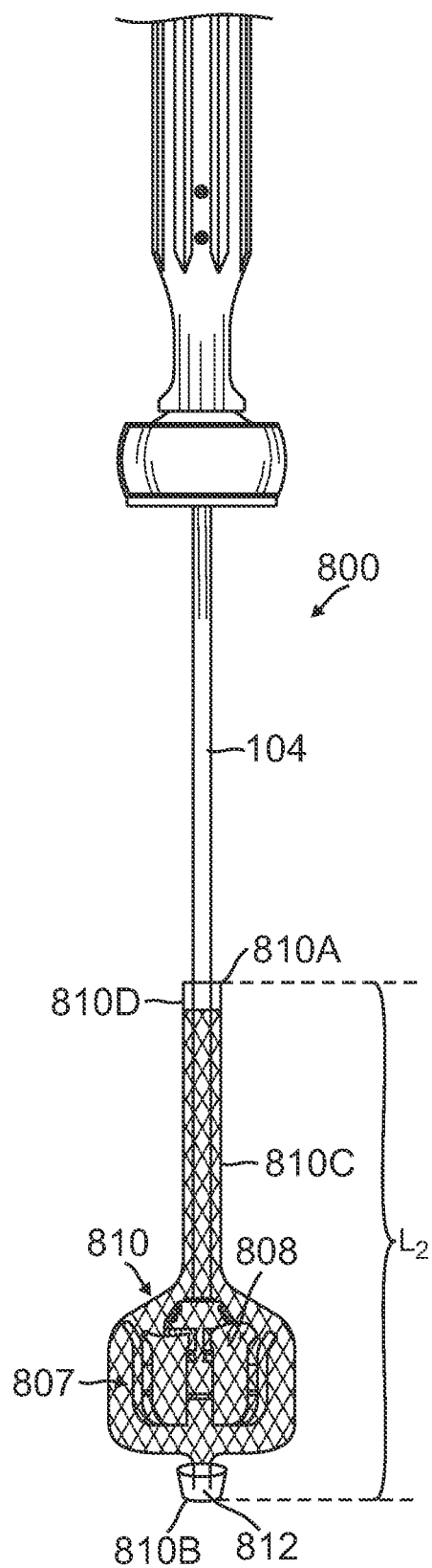
FIGS. 8A-8B show the heart valve sizer with a basket cover completely covering the sizing element, according to yet another example.
Figure 8B:
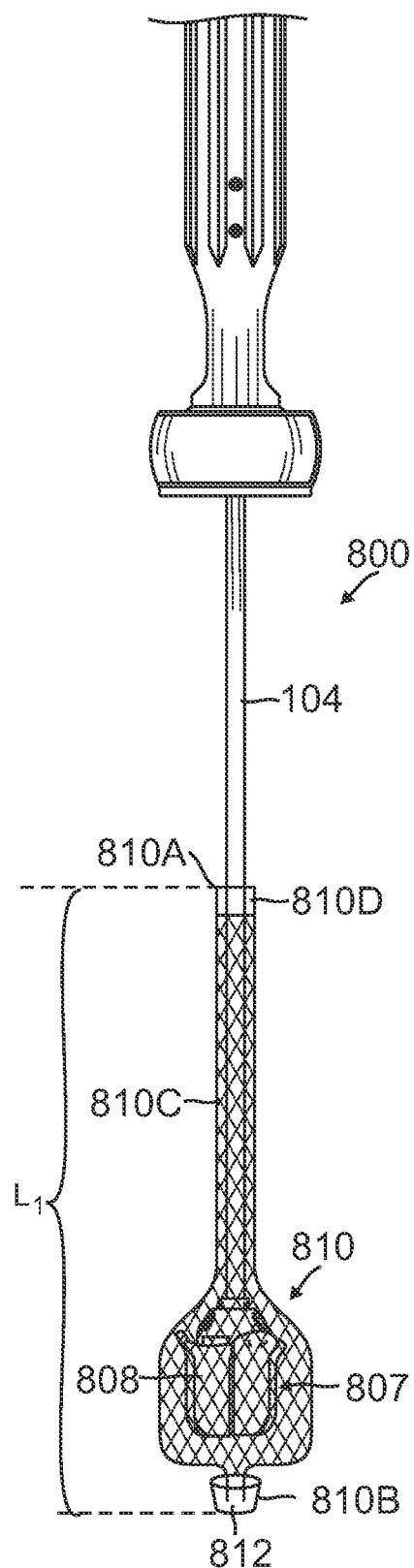

FIGS. 8A-8B show another example of a covered valve sizer 800, in which a basket-shaped sizer cover 810 is made of shape memory alloy wires that completely cover, surround, and/or envelop the sizing element 807. The proximal end 810A of the sizer cover 810 can include a collar 810D around the shaft 104. The distal end 810B of the sizer cover is configured to surround and cover the entire sizing element 807 and can include a crimped cap 812 at the distal end 810B of the sizer cover 810. The cap 812 is configured to crimp the distal end 810B of the sizer cover 810 so that it does not slip off the sizing element 807 as the sizing element 807 is expanded and contracted. In this manner, the sizer cover 810 remains completely covering the sizing element 807 during use (e.g., the sizing element 807 remains completely within the sizer cover 810 as the sizing element is expanded and contracted).

Radial expansion of the sizing element 807 shortens the sizer cover 810 from a first length $L_1$ (FIG. 8B) corresponding to a contracted position to a second, shortened length $L_2$ (FIG. 8A) corresponding to an expanded position. The collar 810D can have an inner diameter that is slightly larger than the outer diameter of the shaft 104, thus allowing the collar 810D to slide freely on the shaft 104 during the radial contraction and expansion of the sizing element 807. Thus, collar 810D of the sizer cover 810 may move longitudinally along the shaft 104 as the sizing element 807 expands and contracts, to allow the covered sizing petals 808 to expand radially outward from the shaft 104.

In yet another example of a sizer cover for an adjustable heart valve sizer according to the present disclosure, and as shown in FIGS. 9-10, a collar 950 is provided that slidably moves longitudinally with respect to the shaft 904 of an adjustable heart valve sizer. (It should be noted that one embodiment of a cover is shown in FIG. 10, while only a portion of the cover, the collar 950, is shown in FIG. 9 for clarity.) At the distal end of the shaft 904, the sizing element 907 can include a plurality of sizing petals 908, the proximal edges of which form an outwardly-angled peripheral flange 912. As described above, the peripheral flange 912 is desirably undulating or scalloped so as to have alternating convex and concave segments corresponding to individual petals 908. The sizing petals 908 can surround a hub having a hub cover 909A and a hub bearing or actuator bearing 909. As with other described and/or incorporated examples, the sizing petals 908 are configured to expand radially outward from the shaft 904 when an actuation mechanism is activated.

In the example of FIGS. 9-10, the collar 950 includes a tubular shaft receiving portion 952 and a disk-shaped annular flange 954 extending from or projecting from the distal portion 955 of the collar 950. The shaft receiving portion 952 is configured to surround the shaft 904 and sized to move freely along the shaft 904 (e.g., the shaft 904 can be inserted through or extend through a central bore or opening in the shaft receiving portion 952, as shown). For example, the inner diameter of the shaft receiving portion 952 of the collar 950 can be at least slightly larger than the outer diameter of the shaft 904 so as to allow free motion of the collar 950 with respect to the shaft 904 in the longitudinal direction defined by the shaft 904 (e.g., along the directions indicated by arrow 956). The inner diameter of the shaft receiving portion 952 can be approximately the same size of the outer diameter of the shaft 904, or the inner diameter of the shaft receiving portion 952 can be slightly smaller than the outer diameter of the shaft 904 and can be forced or stretched onto the shaft 904 such that the collar 950 is fixed with respect to the shaft. In some examples, the shaft receiving portion 952 is a cylindrical shaft receiving portion 952. In other examples, the shaft receiving portion 952 can be other shapes, such as having an oval, square, or hexagonal outer surface. The interior of the shaft receiving portion 952 also can be shaped to receive shafts of various cross-sectional shapes, such as round, oval, etc.

The annular flange 954 of the collar 950 can include a plurality of bores or holes 958 extending through the thickness of the annular flange 954. The annular flange 954 can extend substantially perpendicularly from the central bore of the collar 950 surrounding the shaft 904 such that the flange 954 creates a proximal surface and a distal surface. The holes 958 can extend from the proximal surface through to the distal surface, such that the holes 958 each define an axis substantially parallel to the shaft 904. In some examples, the holes 958 are substantially equally spaced around the entire annular flange 954, but other configurations also are possible. For example, the holes 958 can be spaced in pairs such that each respective individual hole 958 in a pair is positioned closer together than are the adjacent pairs of holes 958.

In some examples, the collar 950 can be coupled to the sizing petals 908. For example, as seen in FIG. 10, one or more elongated elements, such as wires 964, are secured to both the collar 950 and one or more of the sizing petals 908. For example, a first end 966 of each of a plurality of wires 964 is threaded through, extended through, looped through, adhered to, tied to, or otherwise coupled to a hole 958 in the annular flange 954 of collar 950. Similarly, a second end 968 of each of a plurality of wires 964 is coupled in any suitable manner (e.g., threaded through, extended through, looped through, adhered to, tied to, or otherwise coupled to) to a hole 970 extending through a sizing petal 908. In this embodiment, the cover is formed by a series of separate elongated elements with circumferential gaps therebetween, though the resulting structure maintains the tent-like guard against structures of the heart becoming entangled with the sizer.

In some examples, each hole 958 in the collar 950 is provided with a wire 964 extending therethrough and/or otherwise coupled to the hole 958. Each of the sizing petals 908 can include one or more holes 970 for securing the second ends 968 of the wires 964. For example, in a specific implementation, each sizing petal 908 includes two holes 970 such that two wires 964 are coupled to each sizing petal 908. The holes 970 are positioned in any suitable position on the sizing petals 908. As shown in FIG. 10, in some examples, the holes 970 are positioned in opposing corners of each individual sizing petal 908 at the proximal end of the sizing petals, adjacent the peripheral flange 912 formed by the sizing petals 908 in aggregate.

The wires 964 can be rigid or semi-rigid wires. For example, the wires 964 should be stiff enough such that when the sizing petals 908 are expanded and contracted, the motion of the sizing petals 908 is transmitted through the wires 964 such that the wires 964 force the collar 950 to move up or down the shaft 904 in response to motion of the sizing petals 908. In some examples, expansion of the sizing petals 908 may pull distally on the wires 964, thereby pulling the collar 950 down the shaft 904 towards the sizing petals 908 (e.g., towards the distal end of the shaft 904). Likewise, contraction of the sizing petals 908 towards the shaft 904 may cause the collar 950 to move up the shaft 904 towards the proximal end of the shaft 904.

The wire 964 and collar 950 combination may serve as a sizer cover, thereby forming a covered heart valve sizer when associated with a heart valve sizer, with the collar 950 being the proximal end of the sizer cover and the second ends 968 of the wires 964 being the distal end of the sizer cover. The wires 964 can be formed of any suitable material, including stainless steel, shape memory alloys, polymers, and/or Nitinol. The wires 964, together, function as a cover or shield to at least substantially prevent the sizing petals 908 from becoming entangled with a patient's chordae tendineae and/or other native structures. For example, the wire/collar sizer cover may allow or force the chordae tendineae to slide off or around the wires 964, thereby preventing the chordae tendineae from getting caught around the sizing petals 908 as they are expanded, contracted, inserted, and/or removed. The wire/collar sizer cover also helps prevent the sizing petals 908 from becoming separated from the sizer body itself. As described in connection with FIGS. 4A-4D, each sizing petal 908 can be coupled to a hub via a plurality of slots within the hub and lever arms coupling the sizing petals 908 to the hub. The presence of the wires 964 and collar 950 may, in some examples, prevent the sizing petals 908 from rocking within the hub slot and potentially disengaging from the hub.

In some examples, additional materials can be included with the wires 964 and collar 950 to provide a sizer cover. For example, a fabric or polymer layer can be provided surrounding the wires 964 to further shield the petals 908 from entanglement with the chordae tendineae or other native heart valve structures.

In yet another example, as shown in FIG. 11, elongated members can be, for example, radially extending legs 1164 rather than wires. Similar to the examples shown in FIGS. 9-10, the heart valve sizer shown in FIG. 11 generally includes a shaft 1104 and a sizing element 1107. The sizing element 1107 includes a plurality of petals 1108 arranged circumferentially about a hub 1109 positioned on the shaft 1104. In the example of FIG. 11, six petals 1108 are shown, but it is within the scope of the present disclosure that fewer or more petals may be utilized. The sizing petals 1108, in combination, form an annular flange 1112 when in the radially contracted position, as shown in FIG. 11. The heart valve sizer preferably includes a sizer cover consisting of a collar 1150 and a plurality of elongated members, such as legs 1164, each extending from a proximal leg end 1166 adjacent the collar 1150 to a distal leg end 1168 adjacent the petals 1108 of the sizing element 1107. In the illustrated embodiment, the legs 1164 comprise thin strips of material each of which has a much larger circumferential dimension than its radial dimension. There are two legs 1164 shown per petal 1108, though only one or more than two are contemplated. This is another example of a cover formed by a series of separate elongated elements.

The elongated legs 1164 and collar 1150 can be composed of any suitable material, such as any suitable metallic or polymeric material, and may be coupled to one another such as by a living hinge (e.g., a thinned area of material at the joint 1166 of the collar 1150 and each leg 1164 that allows the legs 1164 to move in and out with respect to the collar 1150). The opposite end 1168 of the legs 1164 are secured to the petals 1108, such as to the annular flange portion of each of the sizing petals 1108. In some examples, the legs 1164 are secured to the sizing petals 1108 with posts that extend from the distal end 1168 of legs 1164 and insert into holes in the sizing petals 1108 (not shown). As the sizing petals 1108 are radially expanded and contracted, the ends 1168 of the legs 1164 coupled to the petals 1108 also are expanded and contracted. The resulting hinging motion created between the proximal ends 1166 of legs 1164 and the collar 1150 causes the collar 1150 to slide up or down the shaft 1104 in response.

In another variation shown in FIG. 12, the elongated members can be tapered, fan-shaped legs 1264 that create a substantially conical shape when the sizing petals are closed (e.g., in their radially contracted position in FIG. 12). As with FIG. 11, in the example shown in FIG. 12, a heart valve sizer includes a shaft 1204 and a sizing element 1207 having a plurality of sizing petals 1208 circumferentially arranged about a hub 1209. A collar 1250 and a plurality of elongated legs 1264 form a sizer cover that may be configured to help prevent entanglement with a patient's native heart structures, such as the chordae tendineae. Each of the elongated legs 1264 extends from a distal leg end 1268 adjacent the sizing petals 1208 to a proximal leg end 1266 adjacent the collar 1250. Each of the elongated legs 1264 can be tapered in shape, such that the distal end 1268 has approximately the same width as a sizing petal 1208 and narrowing towards the proximal end 1266 of the leg, adjacent the collar 1250. The elongated legs 1264 can spread apart from one another as the sizing petals 1208 are radially expanded, as shown in dashed lines with respect to one of the sizing petals 1208, and form a conical shape enclosing the hub 1209 when the sizing petals 1208 are radially contracted, as shown in FIG. 12.

During assembly of some examples of a heart valve sizer of the present disclosure, a sizer cover (e.g., a sizer cover made of an elastomeric balloon, fabric, a wire and collar combination, wires, legs, and/or a wire mesh material), or a portion thereof, may be associated with a sizer shaft prior to assembling the sizing element at the distal end of the shaft. For example, a collar of a sizer cover may be positioned on the shaft such that the shaft extends through a central bore or opening in the collar, either in a slidable relationship (e.g., the collar being free to move proximally and distally along the longitudinal axis of the shaft) or in a fixed relationship (e.g., the collar being stationary with respect to the shaft, such as by a friction fit, or any other suitable way of fastening or fixing the collar to the shaft). A sizer cover also may be associated with the valve sizer and/or sizer shaft by being coupled to, attached to, mounted on, interfaced with, affixed to, and/or positioned on the sizer shaft.

After associating the sizer cover with the shaft, the sizing element may be fixed at the distal end of the shaft. A distal end of the sizer cover may be moved, stretched, and/or positioned over or around the hub to rest around or adjacent to the sizing element, at least partially covering and/or engaging with the sizing petals of the sizing element in some examples. To ease assembly, in some examples where the distal end of the sizer cover is coupled to the sizing element, the sizing petals may be in a radially expanded position when the distal end of the sizer cover is placed and coupled to, for example, the outer rim of the sizing petals. A canopy of the sizer cover may extend between the proximal and distal ends of the sizer cover. The actuator may be positioned at the proximal end of the shaft either prior to or after the assembly of the sizing element and the sizer cover at or near the distal end of the shaft. The distal end of the sizer cover also may be associated with the sizing element (e.g., a proximal end of the sizing element).

In use in a minimally invasive procedure, the covered valve sizer can be introduced into the patient in any suitable manner, such as between adjacent ribs, without cutting or significantly deflecting the ribs. In some examples, at least one dimension of the delivery profile of the retracted valve sizer may be less than about 19 mm, so that the covered valve sizer can be easily introduced between adjacent ribs into the patient. In some examples, at least one dimension of the delivery profile of the retracted valve sizer is less than about 17 mm. The valve sizer having a sizer cover provides smooth access to and removal from the valvular and sub-valvular spaces of a patient's heart during valve sizing and prevents chordae tendineae entanglement with the outer rims of the sizing element of the covered valve sizer.

To determine the size of a patient's native valve annulus, a surgeon or other operator positions the covered sizing petals within the native valve annulus and activates the actuator until the sizing petals and/or sizer cover contact the valve annulus. For example, in one embodiment the actuator is rotated until the ratchet begins to slip, thus indicating that the sizer has fully engaged the native valve annulus and that a predetermined amount of force is being applied. When in the expanded position, the outer surfaces of opposing sizing petals have a maximum outer dimension of at least 29 mm in some examples. In some examples, the maximum outer diameter of the full expanded sizing element is at least 33 mm. The surgeon or other operator then reads the appropriate valve size using the markings that appear in the window of the actuator. Following the sizing of the annulus, the actuator is then rotated in the opposite direction so that the covered sizing petals move into the retracted position for removing the covered valve sizer from the patient. The covered valve sizer thereby provides smooth entry of the valve sizer into and exit of the valve sizer from, the valvular and sub-valvular spaces of a patient's heart.

Although the present disclosure has been described with reference to specific examples, these examples are illustrative only and not limiting. Many other applications and examples of the present disclosure will be apparent in light of this disclosure and the following claims. The full scope of the invention should thus be determined primarily with respect to the claims appended to this disclosure, along with the full scope of equivalents to which those claims are legally entitled.

We claim:

1. A heart valve sizer, comprising:
   a handle;
   a shaft extending distally from the handle to a distal end;
   a distal sizing element coupled to the distal end of the shaft, the sizing element having a larger diameter than the shaft, wherein the sizing element is size-adjustable between a first, radially-retracted configuration and a second, radially-expanded configuration; and a sizer cover having a proximal end and a distal end, the proximal end being coupled to the shaft at a location proximal to the sizing element and the distal end extending to and widening to a larger diameter at a location on the sizing element, the sizer cover comprising a plurality of separate elongated wires each coupled to both the shaft and the sizing element so as to provide an aggregate conical guard against entanglement of the sizing element with structures of a human heart, and the distal ends of the wires are configured to expand and contract in response to conversion of the sizing element between its first, radially-retracted configuration and its second, radially-expanded configuration.

2. The heart valve sizer of claim 1, wherein the distal ends of the wires are coupled to a proximal end of the sizing element.

3. The heart valve sizer of claim 1, wherein the sizing element comprises a plurality of sizing petals that are generally in contact with one another in the first, radially-retracted configuration and separate in the second, radially-expanded configuration.

4. The heart valve sizer of claim 3, wherein the distal ends of at least two wires are coupled to each petal.

5. The heart valve sizer of claim 3, wherein the sizing petals together define a distal cylindrical exterior and a proximal flange extending outward from the cylindrical exterior of the sizing element in the first, radially-retracted configuration, and the distal ends of the wires are each coupled to a proximal flange of one of the sizing petals.

6. The heart valve sizer of claim 5, wherein the distal ends of the wires are each coupled to a hole through a proximal flange of one of the sizing petals.

7. The heart valve sizer of claim 3, wherein the sizer cover comprises a collar slidable on the shaft to which the proximal ends of the wires are coupled.

8. The heart valve sizer of claim 1, wherein the sizer cover comprises a collar slidable on the shaft to which the proximal ends of the wires are coupled.

9. The heart valve sizer of claim 1, further including a fabric or polymer layer surrounding each of the wires.

10. The heart valve sizer of claim 1, wherein the wires are polymeric.

11. A heart valve sizer, comprising:
a handle;
a shaft extending distally from the handle to a distal end;
a distal sizing element coupled to the distal end of the shaft, the sizing element having a larger diameter than the shaft, wherein the sizing element is size-adjustable between a first, radially-retracted configuration and a second, radially-expanded configuration; and
a sizer cover having a proximal end and a distal end, the proximal end being coupled to the shaft at a location proximal to the sizing element and the distal end extending to and widening to a larger diameter at a location on the sizing element, the sizer cover comprising a plurality of separate elongated legs formed by strips of material each of which has a larger circumferential dimension than a radial dimension, each leg being coupled to both the shaft and the sizing element so as to provide an aggregate conical guard against entanglement of the sizing element with structures of a human heart, and the distal ends of the legs are configured to expand and contract in response to conversion of the sizing element between its first, radially-retracted configuration and its second, radially-expanded configuration.

12. The heart valve sizer of claim 11, wherein the distal ends of the legs are coupled to a proximal end of the sizing element.

13. The heart valve sizer of claim 11, wherein the sizing element comprises a plurality of sizing petals that are generally in contact with one another in the first, radially-retracted configuration and separate in the second, radially-expanded configuration.

14. The heart valve sizer of claim 13, wherein the distal ends of at least two legs are coupled to each petal.

15. The heart valve sizer of claim 13, wherein each leg is tapered in shape, such that a distal end thereof has approximately the same width as a sizing petal and the leg narrows towards a proximal end thereof adjacent the collar.

16. The heart valve sizer of claim 13, wherein the sizing petals together define a distal cylindrical exterior and a proximal flange extending outward from the cylindrical exterior of the sizing element in the first, radially-retracted configuration, and the distal ends of the legs are each coupled to a proximal flange of one of the sizing petals.

17. The heart valve sizer of claim 11, wherein the sizer cover comprises a collar slidable on the shaft to which the proximal ends of the legs are coupled.

18. The heart valve sizer of claim 17, wherein the legs are coupled to the collar at living hinges.

19. The heart valve sizer of claim 11, further including a fabric or polymer layer surrounding each of the legs.

20. The heart valve sizer of claim 11, wherein the legs are polymeric.

* * * * *